United States Patent
Boonn et al.

(10) Patent No.: US 12,165,764 B2
(45) Date of Patent: Dec. 10, 2024

(54) SYSTEM AND METHOD FOR OPTIMIZING RESOURCE ALLOCATION

(71) Applicant: RAD AI, Inc., Berkeley, CA (US)

(72) Inventors: William Boonn, Berkeley, CA (US);
Gregory Couch, Berkeley, CA (US);
John Paulett, Berkeley, CA (US);
Woojin Kim, Berkeley, CA (US);
Jeffrey Chang, Berkeley, CA (US);
Doktor Gurson, Berkeley, CA (US)

(73) Assignee: RAD AI, Inc., San Francisco, CA (US)

( * ) Notice: Subject to any disclaimer, the term of this patent is extended or adjusted under 35 U.S.C. 154(b) by 0 days.

(21) Appl. No.: 18/374,535

(22) Filed: Sep. 28, 2023

(65) Prior Publication Data
US 2024/0112790 A1  Apr. 4, 2024

Related U.S. Application Data

(60) Provisional application No. 63/411,351, filed on Sep. 29, 2022.

(51) Int. Cl.
*G06Q 10/00* (2023.01)
*G06Q 10/1093* (2023.01)
*G16H 40/20* (2018.01)

(52) U.S. Cl.
CPC ......... *G16H 40/20* (2018.01); *G06Q 10/1097* (2013.01)

(58) Field of Classification Search
CPC ....................................... G06Q 10/1093–1097
See application file for complete search history.

(56) References Cited

U.S. PATENT DOCUMENTS

| | | | |
|---|---|---|---|
| 9,727,829 B2 | 8/2017 | Bollapragada et al. | |
| 10,402,426 B2* | 9/2019 | Baldwin | G06Q 50/01 |
| 11,308,434 B1* | 4/2022 | Kalenda | G06Q 10/0635 |
| 11,531,939 B1 | 12/2022 | Yang | |
| 2003/0103415 A1* | 6/2003 | Bates | G06Q 10/109 368/28 |

(Continued)

OTHER PUBLICATIONS

Overbooking in Medical Clinics: Do or Don't? Dec. 23, 2015 | By Peter Kendall, Vice-président ventes et commercialisation https://blog.petal-health.com/overbooking-in-medical-clinics (Year: 2015).*

*Primary Examiner* — Hafiz A Kassim
*Assistant Examiner* — Scott M Ross
(74) *Attorney, Agent, or Firm* — Jeffrey Schox

(57) ABSTRACT

A system for optimizing resource allocation includes and/or interfaces with: a set of contextual data sources; a decision-making subsystem; and a set of schedules. Additionally or alternatively, the system can optionally include and/or interface with a set of user interfaces, memory, a set of data collection, and/or any other suitable components. A method for resource optimization includes: receiving a set of inputs; and processing the set of inputs and/or contextual data with a set of models to produce a set of schedules. Additionally or alternatively, the method can include any or all of: training the set of models; pre-processing the set of inputs to supplement the set of contextual data; dynamically adjusting the set of schedules; triggering a set of actions based on the set of schedules; updating the set of models; and/or any other processes.

19 Claims, 18 Drawing Sheets
(9 of 18 Drawing Sheet(s) Filed in Color)

(56) References Cited

U.S. PATENT DOCUMENTS

| | | | |
|---|---|---|---|
| 2006/0195339 A1 | 8/2006 | Backhaus et al. | |
| 2007/0156456 A1 | 7/2007 | McGillin et al. | |
| 2008/0126948 A1* | 5/2008 | Daniels | G06Q 10/107 715/751 |
| 2009/0055236 A1* | 2/2009 | O'Sullivan | G06Q 10/1095 705/7.19 |
| 2009/0112677 A1 | 4/2009 | Rhett | |
| 2009/0193341 A1* | 7/2009 | Murray | G06Q 10/107 715/751 |
| 2010/0161367 A1* | 6/2010 | Keohane | G06Q 10/109 705/7.19 |
| 2010/0332281 A1 | 12/2010 | Horvitz et al. | |
| 2011/0022438 A1* | 1/2011 | Lian | G06Q 10/06 705/7.18 |
| 2011/0153506 A1 | 6/2011 | Patterson | |
| 2011/0184772 A1* | 7/2011 | Norton | G06Q 10/06311 707/E17.084 |
| 2011/0184943 A1* | 7/2011 | Norton | G06Q 10/02 707/723 |
| 2014/0006079 A1* | 1/2014 | Keohane | G06Q 10/1093 705/7.19 |
| 2014/0089320 A1* | 3/2014 | Baldwin | G06F 16/284 707/748 |
| 2014/0164364 A1 | 6/2014 | Cosgrove et al. | |
| 2015/0067545 A1* | 3/2015 | Griffin | G06Q 10/1095 715/758 |
| 2015/0142895 A1* | 5/2015 | Beran | G06Q 10/0631 709/206 |
| 2016/0034855 A1* | 2/2016 | Guy | G06Q 10/1095 705/7.19 |
| 2016/0180256 A1* | 6/2016 | Renaud | G06Q 10/02 705/5 |
| 2016/0253462 A1 | 9/2016 | Zhong et al. | |
| 2016/0267439 A1* | 9/2016 | Bitran | G06Q 10/1095 |
| 2016/0292651 A1* | 10/2016 | Bathiya | G06Q 10/1095 |
| 2017/0147960 A1 | 5/2017 | Jahagirdar | |
| 2017/0200101 A1 | 7/2017 | Kumar et al. | |
| 2017/0333779 A1* | 11/2017 | El Labban | A63B 71/0616 |
| 2018/0247273 A1 | 8/2018 | Tamma et al. | |
| 2018/0261319 A1 | 9/2018 | Bowie et al. | |
| 2018/0301218 A1 | 10/2018 | Bochaton | |
| 2019/0180868 A1 | 6/2019 | Makram et al. | |
| 2019/0279762 A1 | 9/2019 | Campbell et al. | |
| 2019/0303878 A1* | 10/2019 | Megahed | G06Q 10/1095 |
| 2020/0005247 A1* | 1/2020 | Randall | G06Q 10/1095 |
| 2020/0356677 A1 | 11/2020 | Alexander et al. | |
| 2020/0411170 A1 | 12/2020 | Brown et al. | |
| 2021/0117929 A1* | 4/2021 | Lewbel | G06Q 10/1095 |
| 2022/0180328 A1* | 6/2022 | Shetty | G06Q 10/1093 |
| 2022/0335339 A1 | 10/2022 | Vegas Santiago et al. | |
| 2022/0383265 A1* | 12/2022 | Dhumal | G06F 40/216 |
| 2022/0398546 A1* | 12/2022 | Lightbody | G06F 3/0482 |
| 2023/0019856 A1* | 1/2023 | Lara Maldonado | G06Q 10/063112 |
| 2023/0077130 A1* | 3/2023 | Matsuoka | H04L 67/306 |
| 2023/0147297 A1* | 5/2023 | Ban | G06Q 10/109 705/7.19 |
| 2023/0196301 A1* | 6/2023 | Loftus | G06Q 10/109 705/7.19 |
| 2023/0238123 A1* | 7/2023 | Narumanchi | G16H 40/20 705/2 |

\* cited by examiner

SYSTEM AND METHOD FOR OPTIMIZING RESOURCE ALLOCATION

CROSS-REFERENCE TO RELATED APPLICATIONS

This application claims the benefit of U.S. Provisional Application No. 63/411,351, filed 29 Sep. 2022, which is incorporated in its entirety by this reference.

TECHNICAL FIELD

This invention relates generally to the radiology and healthcare fields, and more specifically to a new and useful system and method for optimizing resource allocation in the radiology and healthcare fields.

BACKGROUND

Resource allocation in various environments is a complicated task. Generally, an ideal resource allocation may minimize resource downtime, or times in which such resources are idle, while also ensuring that conflicts do not exist between different tasks (e.g., for a resource that is limited to handling one task at any given time). In many cases, to allocate these resources, various a priori defined assumptions may be used in an attempt to optimize such an allocation. For example, these a priori defined assumptions may include assumptions about the amount of time that is needed to complete a task, assumptions about a maximum amount of work that a resource can perform over a given amount of time, or the like. However, these a priori defined assumptions may lead to significant underutilization of resources, as many tasks may be completed in less time than an assumed amount of time that is used in allocating these resources. Further, various resource allocation techniques that focus on the allocation of a first set of resources may not take into account resource allocation and utilization of other related resources, which may create bottlenecks and/or resource utilization conflicts, and otherwise result in a resource allocation that does not fully utilize the available resources and/or results in a scheduling conflict that can have adverse effects on resource utilization in an environment.

Thus, there is a need to create a new and useful system and method for optimizing resource allocation in the radiology and healthcare fields.

BRIEF SUMMARY

Certain embodiments provide a computer-implemented method for optimizing resource allocation. An example method generally includes receiving scheduled resource allocation data for a first set of resources in a computing environment and contextual data associated with the scheduled resource allocation data, generating, using a machine learning model, an optimized allocation of the first set of resources in the computing environment and a second set of resources in the computing environment based on the scheduled resource allocation data and contextual data, and allocating the first set of resources and the second set of resources in the computing environment based on the generated optimized allocation.

Additional or alternative embodiments provide a computer-implemented method for optimizing a set of schedules associated with a facility and/or a set of patients and/or a set of users based on contextual data, and iteratively adjusting the set of schedules as new information is received.

Additional or alternative embodiments provide a computer-implemented method for optimizing the distribution of cases within and among radiologist schedules (e.g., worklists) such that radiologists are assigned cases that are any or all of: optimized for their experience, commensurate in complexity with their experience and/or their colleagues, reflective of their working environment (e.g., who they are scheduled with), and/or otherwise optimized.

Additional or alternative embodiments provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer-readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

BRIEF DESCRIPTION OF THE FIGURES

The appended figures depict certain aspects of one or more embodiments and are therefore not to be considered limiting of the scope of this disclosure.

The patent or application file contains at least one drawing executed in color. Copies of this patent or patent application publication with color drawing(s) will be provided by the Office upon request and payment of the necessary fee.

To facilitate understanding, identical reference numerals have been used, where possible, to designate identical elements that are common to the drawings. It is contemplated that elements and features of one embodiment may be beneficially incorporated in other embodiments without further recitation.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Aspects of the present disclosure provide apparatuses, methods, processing systems, and computer-readable mediums for optimizing resource allocation across different groups of resources.

1. Overview

Figure 1:
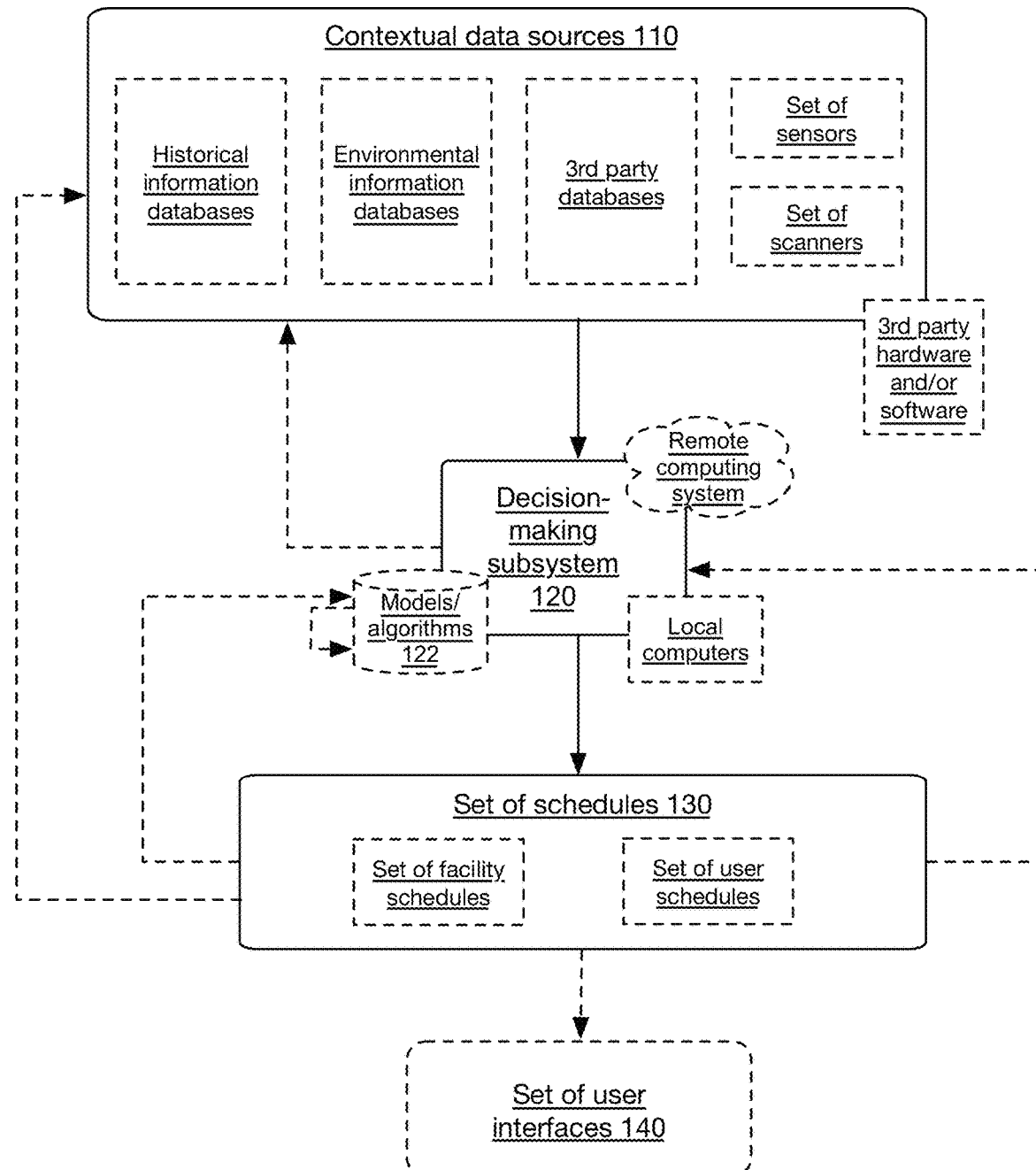
FIG. 1 depicts a schematic of a system for optimizing resource allocation.

As shown in FIG. 1, a system 100 for optimizing resource allocation includes and/or interfaces with: a set of contextual data sources no; a decision-making subsystem 120; and a set of schedules 130. Additionally or alternatively, the system 100 can optionally include and/or interface with a set of user interfaces 140, memory (e.g., as implemented in the contextual data sources), a set of data collection devices (e.g., imaging devices/scanners, vital sign measurement devices, etc.), and/or any other suitable components. Further additionally or alternatively, the system 100 can include and/or interface with any or all of the systems, components, embodiments, and/or examples as described in any or all of: U.S. application Ser. No. 17/649,213, filed 28 Jan. 2022; U.S. application Ser. No. 16/688,623, filed 19 Nov. 2019, now issued as U.S. Pat. No. 11,610,667; U.S. application Ser. No. 17/020,593, filed 14 Sep. 2020, now issued as U.S. Pat. No. 11,342,055; U.S. application Ser. No. 17/690,751, filed 9 Mar. 2022, now issued as U.S. Pat. No. 11,615,890; and U.S. application Ser. No. 18/215,354, filed 28 Jun. 2023; each of which is incorporated herein in its entirety by this reference.

Figure 2:
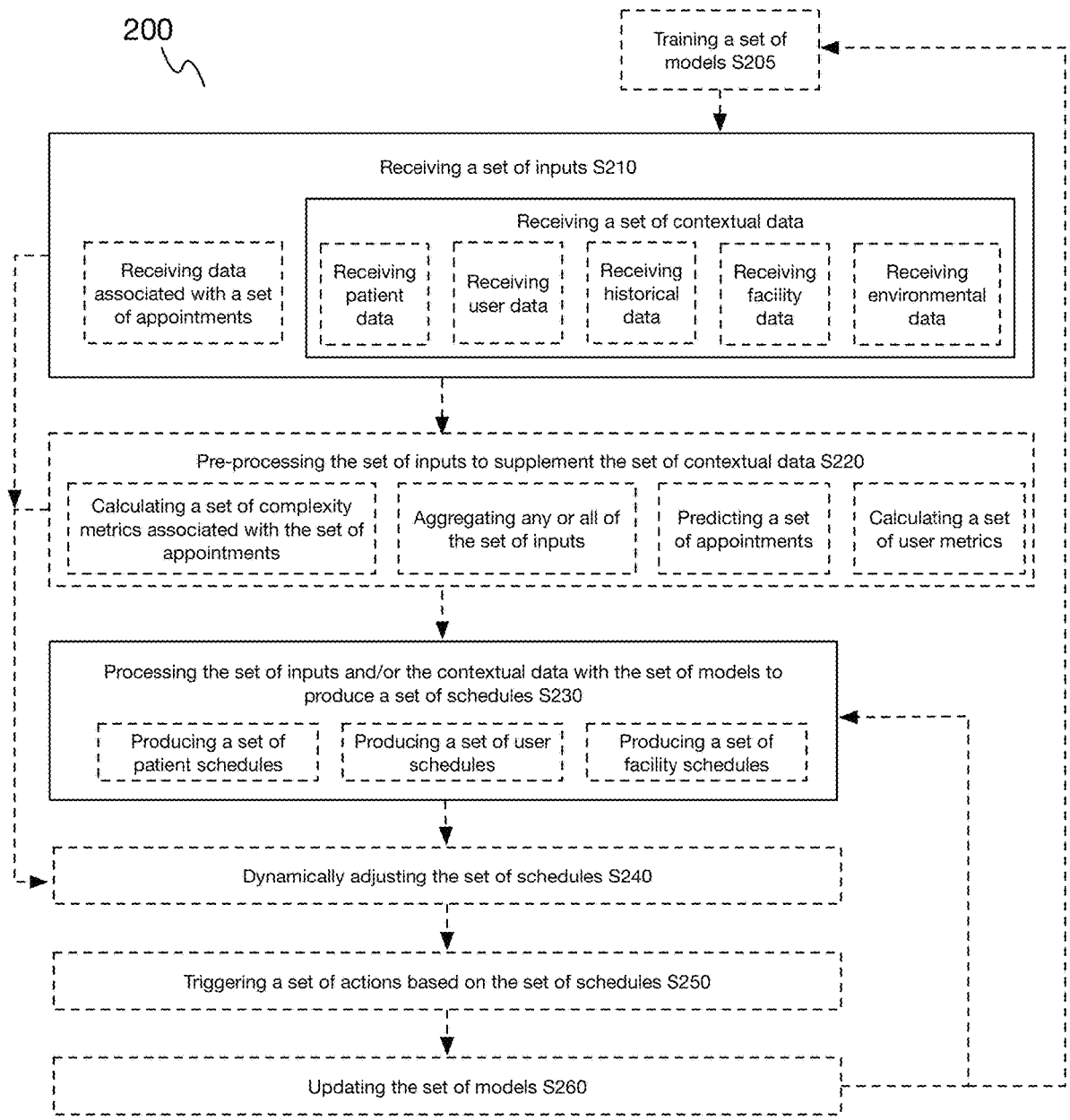
FIG. 2 depicts a schematic of a method for optimizing resource allocation.

As shown in FIG. 2, a method 200 for resource optimization includes: receiving a set of inputs S210; and processing the set of inputs and/or contextual data with a set of models to produce a set of schedules S230. Additionally or alternatively, the method 200 can include any or all of: training the set of models S205; pre-processing the set of inputs to supplement the set of contextual data S220; dynamically adjusting the set of schedules S240; triggering a set of actions based on the set of schedules S250; updating the set of models S260; and/or any other processes. Further additionally or alternatively, the method 200 can include and/or interface with any or all of the methods, processes, embodiments, and/or examples as described in any or all of: U.S. application Ser. No. 17/649,213, filed 28 Jan. 2022; U.S. application Ser. No. 16/688,623, filed 19 Nov. 2019, now issued as U.S. Pat. No. 11,610,667; U.S. application Ser. No. 17/020,593, filed 14 Sep. 2020, now issued as U.S. Pat. No. 11,342,055; U.S. application Ser. No. 17/690,751, filed 9 Mar. 2022, now issued as U.S. Pat. No. 11,615,890; and U.S. application Ser. No. 18/215,354, filed 28 Jun. 2023; each of which is incorporated herein in its entirety by this reference.

The method 200 is preferably performed with a system 100 as described above but can additionally or alternatively be performed with any other suitable system(s).

Aspects of the present disclosure provide techniques for optimizing resource allocation for a facility and/or set of users (e.g., radiologists, technologists, other facility staff, etc.) and/or a set of patients. Generally, a schedule defining usage of a first set of resources is received and processed by one or more machine learning models to generate an optimized allocation of a first set of resources and optionally any number of additional resources (e.g., a related second set of resources, an unrelated second set of resources, etc.). This optimized allocation of the first set of resources may, for example, attempt to minimize downtime for the first set of resources and allow for unscheduled utilization of the first set of resources.

Additionally and optionally, the optimized allocation of a second set of resources may attempt to minimize downtime for the first set of resources as well as bottlenecks that may arise due to the complexity of analysis processes on outputs generated by the first set of resources and subsequent outputs provided to the second set of resources for analysis. By using machine learning models to allocate processing resources in an environment, aspects of the present disclosure may optimize the allocation of these resources to minimize the amount of time these resources are idle and minimize bottlenecks downstream from a first set of resources that may result from an unoptimized allocation of resources.

In some variants, to optimize resource utilization, including maximizing the amount of time resources are used, minimizing idle time for resources in the environment, and minimizing delays caused by unoptimized resource allocation, the system (e.g., set of multiple machine learning models) can generate an optimized allocation of resources based on scheduled resource allocation data and contextual data about the tasks to be executed within the computing environment. For example, in a medical imaging environment in which these machine learning models are used to allocate resources, the contextual data can include information about the states of users utilizing the resources, such as information about a patient, the type of procedure for which imaging is being captured, a complexity involved, information about the imaging resource operator (e.g., experience, relative speed in which an operator can prepare a patient for a scan, etc.), a speed at which resources in the medical imaging environment can capture and analyze imaging for the patient, state of the previous exams scheduled and performed, external factors (e.g., weather, traffic patterns, and other information that may influence a rate at which scheduled appointments are missed), historical information (e.g., trends associated with different days and/or times of year at the facility), and the like.

Additionally or alternatively, aspects of the present disclosure can be otherwise suitably configured and/or utilized.

2. Benefits

In a first set of variants, the technology confers the benefit of optimizing the scheduling of multiple appointment slots through the processing and/or prediction of various information related to said scheduling. As elaborated on below, resource allocation can be a complicated task that involves many inter-related considerations. For example, in a medical imaging environment, resources to be allocated may include the imaging devices that generate imaging for various patients and analysis resources (e.g., processors, radiologists, etc.) that ingest the generated imaging and generate diagnoses for various patients. While a priori defined time blocks (e.g., predetermined time blocks, statically determined time blocks, etc.) may be used to schedule resource utilization in this environment, such a priori defined scheduling may result in a resource allocation that does not make optimal use of the resources in the medical imaging environment, nor dynamically adapt to changing conditions in the medical imaging environment. For example, some resource allocation systems may assume a priori that an imaging device, such as a magnetic resonance imaging (MRI) machine or a computed tomography (CT) machine, can be used for a single patient in 45-minute blocks of time. However, capturing imaging for a patient may take less time than this a priori defined time block or may take more time than this a priori time block due to the complexity of the scan. For example, obtaining an MRI examination of brain in a young patient with headache may take less time than obtaining the same examination for an ICU patient to look for infection. Thus, using a priori defined blocks of time to schedule resource utilization may result in significant downtime during which an imaging device could otherwise be put to productive use as well as times in which the complexity of a case causes cascading delays to the resource scheduling in the medical imaging environment.

Additionally or alternatively, the complexity of a scan or other appointment can include: evaluating a set of scan images with a set of computer vision processes (e.g., computer vision software) to produce a complexity score; utilizing the computer vision process along with contextual data (e.g., metadata, whether or not the patient is claustrophobic, whether or not the patient is intubated, whether the patient has an age above a threshold or below a threshold, etc.) to produce a complexity score; and/or otherwise producing a complexity score.

Still further, scheduled resource utilization for a first group of resources may trigger the scheduling of a second group of resources downstream from the first group of resources. For example, scheduling imaging procedures using the imaging devices in the medical imaging environment may trigger corresponding scheduling of image analysis procedures that process captured images and generate patient diagnoses or queuing of the captured images for processing and scheduling of specific resources to process these captured images. Using these a priori defined blocks of time to schedule usage of the first group of resources may similarly result in significant downtime during which processing resources could be otherwise put to productive use as well as times in which the complexity of a case causes cascading delays to completion of image analysis procedures on subsequently captured imaging.

In a set of examples, for instance, the system and/or method utilize contextual information from various points in time and/or time scales, along with a decision-making subsystem (e.g., set of trained models), to optimize and dynamically adjust (e.g., move around, introduce new availability, etc.) schedules (e.g., appointment slots for patients, cases to be reviewed by a radiologist such as according to a worklist, etc.) associated with a set of tasks (e.g., scan, doctor visit, etc.) and/or individuals (e.g., patients, radiologists, etc.) and/or facilities (e.g., imaging center, healthcare facility, hospital, emergency room, etc.).

In a second set of variants, additional or alternative to the first, the technology confers the benefit of optimally crafting a set of worklists for each of a set of radiologists, and distributing a total volume of cases (e.g., actual cases, predicted cases, etc.) among a set of worklists, wherein the worklists can be optimized with regard to any or all of: including cases of varying complexity within each radiologist's worklist (e.g., to increase a fairness among the worklists of multiple radiologists, to prevent a radiologist from picking only the easiest cases to work on, etc.); including a volume and/or complexity of cases in the worklists that best matches the radiologist's efficiency and/or level of experience and/or working conditions; producing worklists that best match a predicted volume of cases for that time period; and/or otherwise optimizing the production of a set of worklists.

Additionally or alternatively, optimally crafting the set of worklists can further function to improve an accuracy of prediction associated with a set of cases to be performed during the time period associated with the worklists, such that the system and method enable a predictive matching of supply and demand for the radiology group (equivalently referred to herein as demand forecasting). In a set of variants, for instance, the system and method enable a volume and/or type of cases to be predicted (e.g., with a set of models as described below, based on historical trends, based on dynamically changing information, etc.), wherein this accurate prediction enables cases to be fairly and optimally distributed among radiologists. In a specific example, this optimization prevents matching a case with a first radiologist who ultimately deems that the case is too complex, which requires the case to be re-assigned to a second radiologist, leading to delays and wasted time.

In a third set of variants, additional or alternative to those described above, the technology confers the benefits necessarily rooted in computer technology, specifically with respect to improvements in the training and utilization of machine learning models specific to resource optimization. In specific examples, for instance, the system and method utilize multiple machine learning models of multiple types of architectures, each of the set of models specifically trained (e.g., with supervised learning, with semi-supervised learning, with unsupervised learning, etc.) to determine a particular intermediate output (e.g., prediction of missed appointments, duration of appointment, etc.) utilized in optimizing the schedule(s) of a facility and/or set of users.

Additionally or alternatively, the technology can confer any other suitable benefits.

3. System 100

As shown in FIG. 1, a system 100 for optimizing resource allocation includes and/or interfaces with: a set of contextual data sources no; a decision-making subsystem 120; and a set of schedules 130. Additionally or alternatively, the system 100 can optionally include and/or interface with a set of user interfaces 140, memory (e.g., as implemented in the contextual data sources), a set of data collection devices (e.g., imaging devices/scanners, vital sign measurement devices, etc.), and/or any other suitable components. Further additionally or alternatively, the system 100 can include and/or interface with any or all of the systems, components, embodiments, and/or examples as described in any or all of: U.S. application Ser. No. 17/649,213, filed 28 Jan. 2022; U.S. application Ser. No. 16/688,623, filed 19 Nov. 2019, now issued as U.S. Pat. No. 11,610,667; U.S. application Ser. No. 17/020,593, filed 14 Sep. 2020, now issued as U.S. Pat. No. 11,342,055; U.S. application Ser. No. 17/690,751, filed 9 Mar. 2022, now issued as U.S. Pat. No. 11,615,890; and U.S. application Ser. No. 18/215,354, filed 28 Jun. 2023; each of which is incorporated herein in its entirety by this reference.

The system 100 preferably functions to perform any or all of the processing associated with the method 200, thereby enabling resource allocation to be optimized in one or more ways and for one or more use cases. Additionally or alternatively, the system 100 can function to improve an experience for one or more users (e.g., patients, radiologists, healthcare professionals, etc.), improve an efficiency of scheduling, improve a predictive accuracy associated with a schedule and/or workload and/or case, maintain and/or utilize a set of data (e.g., contextual data), and/or confer any other advantages.

In a first set of variants, for instance, optimizing resource allocation includes optimizing the scheduling of a set of appointments for a set of users (e.g., patients) and/or the tasks to be performed by another set of users (e.g., radiologists, technologists, etc.). The scheduling can be associated with a set of particular data collection devices (e.g., MRI scanners, CT scanners, ultrasound scanners, etc.), computers and/or processors (e.g., for performing any or all of the method 200), individuals performing tasks associated with the appointments (e.g., healthcare professionals examining the patient, technicians operating the data collection devices, etc.), and/or any other features or parameters. Optimizing the scheduling of a set of appointments can function to decrease a number and/or occurrence of appointments missed by a patient, decrease an amount of time that a data collection device sits idle (e.g., is unused), decrease an amount of time that an individual (e.g., patient, healthcare professional seeing a patient, radiologist reviewing cases, technologist operating a data collection device, etc.) is kept waiting, increase a likelihood that a late appointment request can be fit into a schedule (e.g., without causing adverse consequences), and/or the scheduling of a set of appointments can be otherwise suitably optimized.

Appointments can refer herein to any or all of: a set of time blocks (e.g., time at which a patient will be scanned, time at which a radiologist will review a study, etc.); a set of tasks (e.g., a scan to be performed for the patient, a scan to be performed by a technologist operating the scanner, a study to be reviewed by a radiologist, etc.); and/or any other information. Appointments can be scheduled (e.g., predetermined), not scheduled (e.g., predicted), or any combination.

In a second set of variants, for instance, optimizing resource allocation includes optimizing the workload (e.g., number of types and cases) for individual radiologists and/or the distribution of cases among a workforce of multiple radiologists. Optimizing these workload(s) and/or matching of cases with radiologists can function to enable any or all of: increased satisfaction of individual radiologists with the distribution and/or order of cases in their workload, increased satisfaction (e.g., sense of fairness) of individual radiologists when comparing their workloads with workloads of their colleagues, increased efficiency of the review of cases by a set of radiologists, and/or any other outcomes.

Additionally or alternatively, resource allocation can be optimized in any suitable way(s) and in any suitable environment(s) (e.g., healthcare-related fields, non-healthcare-related fields, etc.).

3.1 Set of Contextual Data Sources 110

The system 100 preferably includes and/or interfaces with a set of contextual data sources 110, wherein the set of contextual data sources functions to contain information which is utilized by the method 200 in optimizing resource allocation in any number of ways. Additionally or alternatively, the data in the contextual data sources can be used to dynamically adjust schedules (e.g., as the contextual data as updated, as initial appointment predictions are verified and/or deemed incorrect, etc.), predict a volume of cases to be encountered at a facility, and/or can be otherwise suitably used.

The set of contextual data sources preferably includes a set of databases (e.g., stored in memory associated with the decision-making subsystem 120), such as, but not limited to: a set of databases containing historical information; a set of databases containing environmental information; a set of databases containing $3^{rd}$ party information; and/or any other databases.

Historical information (e.g., as further described below) can include, but is not limited to, any or all of: historical information associated with a set of patients (e.g., demographic information [e.g., age, sex, race, etc.], medical history, prior appointment history [e.g., types of scans previously performed, technologists on duty during previous scan(s), radiologist who reviewed previous scan(s), number of missed appointments in their history, average time at which the patient was either early or late or on time to previous appointments, etc.], etc.); historical information associated with a set of radiologists or other facility workers, such as technologists (e.g., average time to generate a report, efficiency metric(s), specialty type, experience level metric (s), average time for technologist to execute a scan, average time technologist spends socializing with the patient prior to and/or during a scan, average time it takes for a technologist to travel between scanners, etc.); historical information associated with the facility (e.g., volume trends associated with time of day that indicate how many patients are scanned at any given time, volume trends associated with day of the week, volume trends associated with month, volume trends associated with environmental conditions such as traffic or weather, scanner health metrics such as age and/or likelihood of breaking down and/or average speed of scan, distance between scanners, etc.); and/or any other information.

In some variants, for instance, historical information associated with the patients (and/or metrics derived based on this historical information, such as metrics calculated with a set of models and/or algorithms) can be used to predict (e.g., with a set of models) temporal parameters associated with coming to an appointment (e.g., whether or not the patient is expected to be late to an appointment, how late a patient is expected to be to an appointment, how long a particular patient's appointment is expected to last, etc.) based on historical trends associated with their attendance of previous appointments and/or predicted trends associated with other information (e.g., demographic information, location information such as distance to the facility, etc.).

In additional or alternative variants, for instance, historical information associated with users at the facility (e.g., radiologists, technologists, etc.) (and/or metrics derived based on this historical information, such as metrics calculated with a set of models and/or algorithms) can be used to determine and/or predict which cases (e.g., studies, images to be analyzed, etc.) and/or distribution of cases should go to which radiologists. In some examples, for instance, the historical information can include radiologist performance data and/or metrics, such as, but not limited to, any or all of those described in U.S. application Ser. No. 17/649,213, filed 28 Jan. 2022, which is incorporated in its entirety by this reference. In specific examples, for instance, cases can be assigned to radiologists based on any or all of: an efficiency rating associated with the radiologist (e.g., average time for the radiologist to process a case, average time for a radiologist to process a case when working with a specific other radiologist or number of other radiologists, etc.), an experience level associated with the radiologist (e.g., number of years practicing, type of certification, type of specialty, etc.), shift information (e.g., when the radiologist is working, who the radiologist is scheduled to work with, etc.), and/or any other metrics.

Environmental information (e.g., as further described below) can include, but is not limited to, any or all of: weather information (e.g., proximal to [e.g., within a predetermined distance of] the facility, weather at the time of an appointment, weather prior to a time of the appointment, snow vs. rain vs. sunshine, etc.), traffic information (e.g., near the facility, prior to an appointment, etc.), and/or any other information.

$3^{rd}$ party information can include, but is not limited to, external database information (e.g., internet information, retrievable environmental information, etc.), information from $3^{rd}$ party hardware and/or software (e.g., sensor data from user devices, sensor data from scanners, data from scanner software that predicts the duration that a scan will last, etc.), and/or any other information.

The set of inputs can further additionally or alternatively include data from the scanner (e.g., images acquired at the scanner during the appointment and forming a study/case, health information associated with the scanner, etc.), data from other sensor systems (e.g., mobile user device data), and/or any other information.

3.2 Decision-Making Subsystem 120

The system includes a decision-making subsystem 120, wherein the decision-making subsystem preferably includes a set of computers, processors, and/or combination of computers and processors configured to perform any or all of the processing associated with the method 200.

The set of computers and/or processors can include, for instance, but are not limited to any or all of: a set of computers and/or processors (e.g., local computers, remote computing subsystems, cloud-based computing subsystems, virtual machines, etc.), associated components (e.g., power sources, data storage sites, etc.), and/or any other components.

Figure 17:
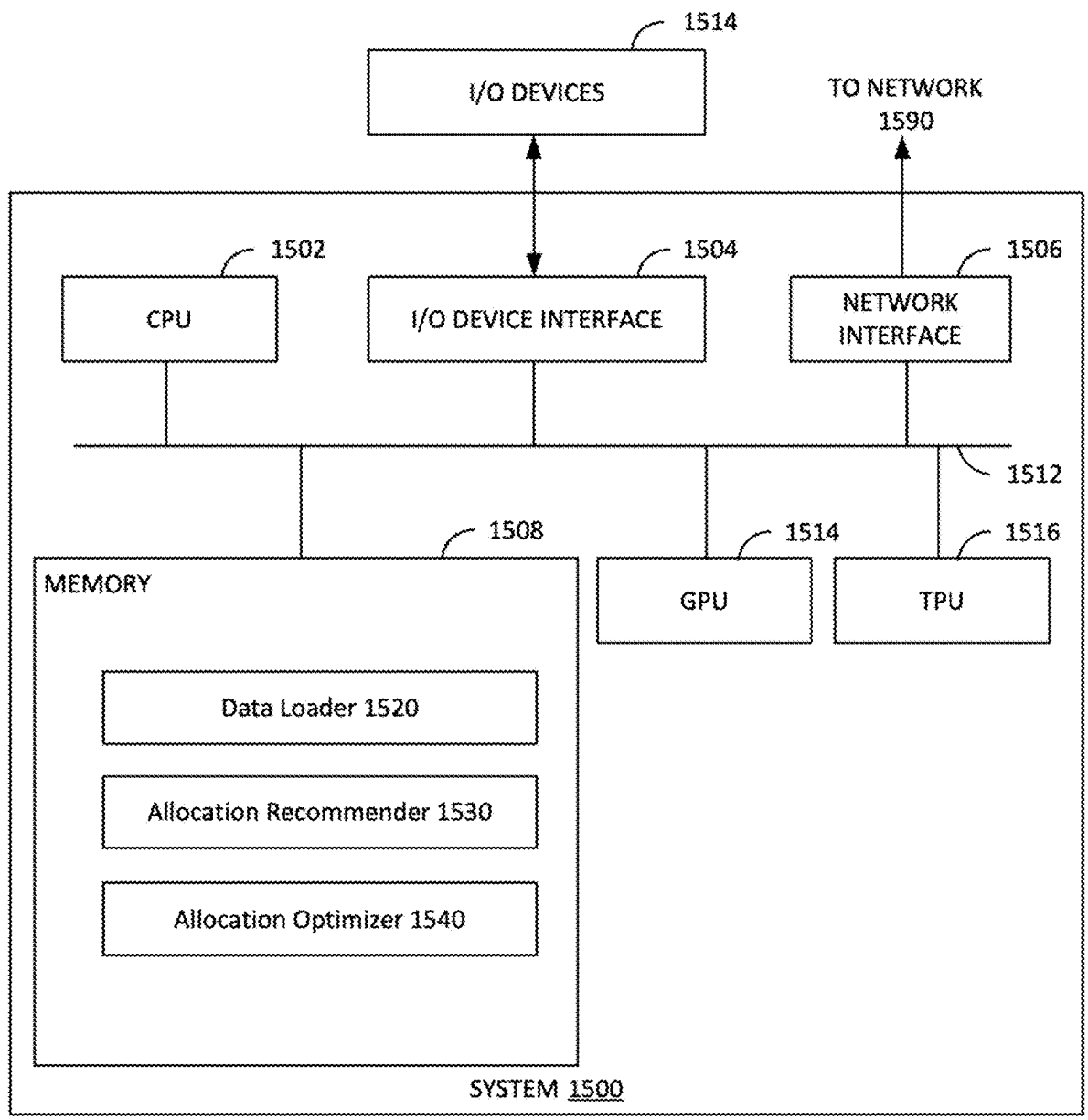
FIG. 17 illustrates an example processing system used to optimize resource allocation.

FIG. 17 illustrates an example processing system 1500 that optimizes resource allocation. For example, system 1500 can include an allocation optimization system as part of and/or all of the decision-making subsystem 110, such as allocation optimization system 300 illustrated in FIGS. 5A-5B.

As shown, system 1500 includes a central processing unit (CPU) 1502, one or more I/O device interfaces 1504 (equivalently referred to herein as user interfaces) that may allow for the connection of various I/O devices 1514 (e.g., keyboards, displays, mouse devices, pen input, etc.) to the system 1500, network interface 1506 through which system 1500 is connected to network 1590 (which may be a local network, an intranet, the internet, or any other group of computing devices communicatively connected to each other), a memory 1508, and an interconnect 1512.

CPU 1502 may retrieve and execute programming instructions stored in the memory 1508. Similarly, the CPU 1502 may retrieve and store application data residing in the memory 1508. The interconnect 1512 transmits programming instructions and application data, among the CPU 1502, I/O device interface 1504, network interface 1504, memory 1508, GPU 1514, and TPU 1516.

CPU 1502 is included to be representative of a single CPU, multiple CPUs, a single CPU having multiple processing cores, and the like.

GPU 1514 is included to be representative of a massively parallel processing unit which can perform various operations in parallel, including, but not limited to, graphics processing, machine learning model training, and/or other operations that can leverage parallelism for completion.

TPU 1516 is included to be representative of a tensor processing unit which can perform various tensor operations, such as those involved in training machine learning models and using machine learning models to generate the predictions and optimizations discussed herein.

It should recognized that in some aspects, processing system 1500 need not include GPU 1514 and/or TPU 1516. GPU 1514 and TPU 1516 may accelerate the training and use of machine learning models; however, CPU 1502 can also or alternatively train and use the machine learning models for various resource optimization tasks as discussed herein.

Memory 1508 is representative of volatile memory, such as a random access memory, or a nonvolatile memory, such as nonvolatile random access memory, phase change random access memory, or the like. As shown, memory 1508 includes data loader 1520, allocation recommender 1530, and allocation optimizer 1540.

Figure 16:
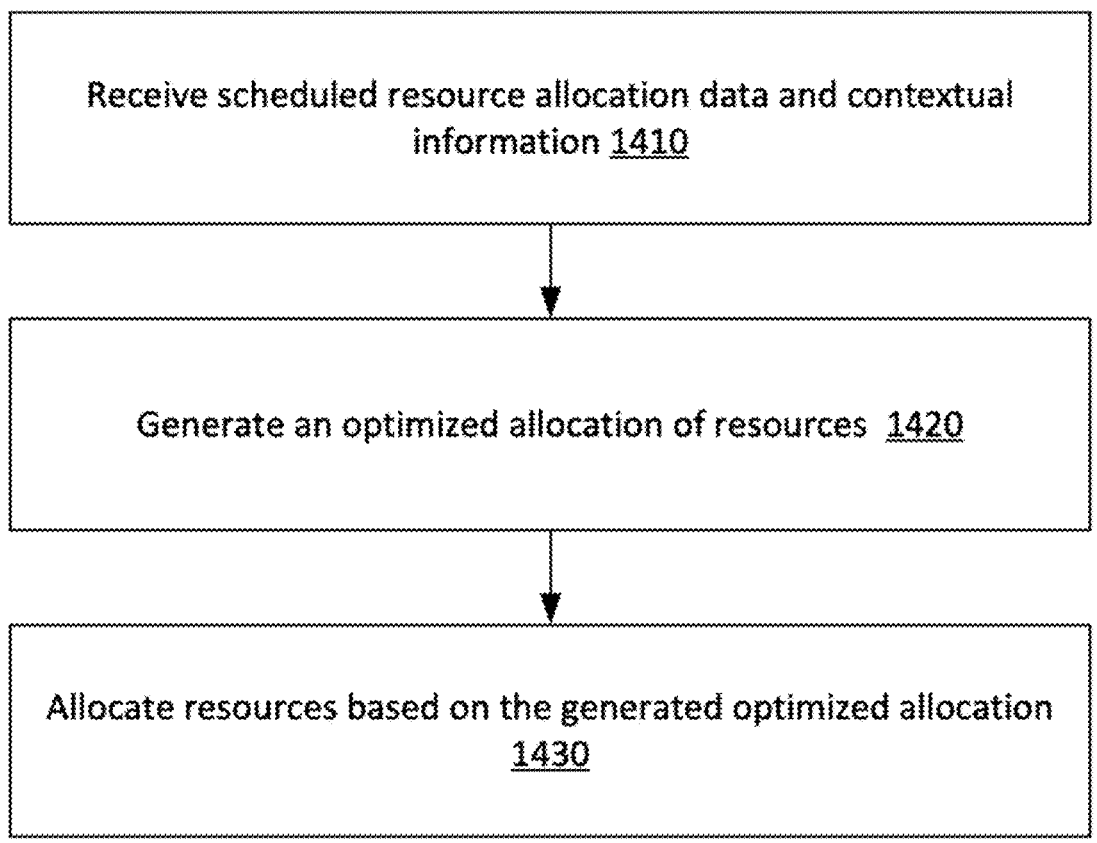
FIG. 16 illustrates a flowchart of a process for optimizing resources in a computing environment using machine learning models.

Data loader 1520 can receive scheduled resource allocation data and contextual data, performing block 1410 shown in FIG. 16.

Allocation recommender 1530 can generate an optimized allocation of resources based on scheduled resource allocation data and contextual data, performing block 151420 shown in FIG. 16.

Allocation optimizer 1540 can allocate resources based on the generated optimized allocation, performing block 1430 shown in FIG. 16.

Additionally or alternatively, the decision-making subsystem 110 can be otherwise suitably configured.

3.21 Set of Models and/or Algorithms 122

The decision-making subsystem 120 preferably includes and/or interfaces with (e.g., executes) a set of models and/or algorithms 122, wherein the set of models and/or algorithms function to produce a set of outputs that are utilized in optimizing resource allocation (e.g., as described below). Additionally or alternatively, the set of models and/or algorithms can be utilized to produce intermediate outputs and/or produce any other information.

The set of models and/or algorithms preferably includes a set of trained (equivalently referred to herein as learned) models and/or algorithms, and further preferably a set of machine learning models (e.g., deep learning models, neural networks, trained regression models, trained classifier models, etc.). Additionally or alternatively, any or all of the decision-making subsystem can implement rule-based tools (e.g., set of rules to be evaluated, rule-based models and/or algorithms, decision trees, lookup tables, etc.), statistical tools (e.g., statistical equations and/or models, etc.), and/or any other tools.

The set of models and/or algorithms can, in some variations, be configured as and/or function as a prediction subsystem (e.g., including one or more machine learning models) and/or an optimization subsystem (e.g., including one or more machine learning models). For instance, the prediction subsystem can predict future resource utilization based on the scheduled resource allocation data (e.g., scheduled set of appointments, tasks determined based on a scheduled set of appointments, etc.) and the contextual data, and the optimization subsystem can use the predictions to re-allocate resources such that the device and computational and/or user resources being allocated are more efficiently used. The optimization sub-model can also create new resource utilization opportunities, which can be used for unscheduled tasks. The prediction subsystem can include one or more models, the optimization subsystem can include one or more models, and/or any number of models can be used for prediction, optimization, and/or the collective functions of prediction and optimization. Additionally or alternatively, the set of models can be otherwise suitably used for any other purposes.

In some variants (e.g., involving appointment scheduling for a set of patients, involving task scheduling for a set of technologists performing tasks during the set of patient appointments, etc.), the resource allocation generated by these machine learning models may include a set of time blocks representing the usage of the resources in the environment and/or features (e.g., duration, start time, end time, location, type of appointment [e.g., type of imaging performed, type of procedure being performed, etc.], type of processing being performed [e.g., which part of the method 200 is being performed], etc.) associated with the set of time blocks (equivalently referred to herein as appointment slots). These time blocks are preferably defined at least in terms of a start time (e.g., when an appointment is scheduled to begin, when processing is scheduled to be performed, etc.) and a duration over which a resource is to be used. Additionally or alternatively, time blocks can be defined by other information (e.g., one or more granular sub-components). For example, a time block may be defined by an arrival time, a time at which a patient enters the room in which a scan will be performed and/or an appointment will be held, the time at which a scan starts, and the like, and the resource allocation generated by these machine learning models may generate an optimized schedule based on predictions of the granular sub-components for each appointment (and thus each scheduled patient). A sequence of the time blocks (e.g., schedule) can be generated and used to allocate resources in the environment.

Because the duration of a time block in an optimized resource allocation plan can be shorter or longer than the duration of an a priori defined scheduled time block (equivalently referred to herein as an initial appointment slot and/or scheduled appointment slot and/or predetermined time slot), gaps may exist between different blocks of time over which the resources are allocated for use. To improve resource utilization in the environment, these gaps may be aggregated into additional blocks of time that can be dynamically allocated as conditions dictate. For example, in a medical imaging environment, these gaps may be aggregated into additional blocks of time that can be used to accommodate additional patients, such as unscheduled patients for which imaging is captured on an emergency basis.

In some aspects of conventional scheduling, for instance, if a patient has a complex condition, a resource reservation for that patient can end after the start time of the next scheduled time block. The prolonged resource utilization can cause cascading delays in subsequent resource utilization. In addition, a patient can be late for a scheduled time block or miss a scheduled time block entirely. Thus, aspects of the present disclosure may also predict the time needed to perform a task (e.g., based on the patient and the complexity of the task, based on historical information associated with the patient's previous scans, according to medical information associated with the patient, associated with a predicted complexity of the scan, etc.) and predict the likelihood that scheduled resource utilization will commence late or will not occur. Based on these predictions, the set of models and/or algorithms discussed herein can dynamically generate updated resource allocations that account for these changes and attempt to maximize resource utilization in the environment (e.g., through iteratively and dynamically updating the schedule of patient appointments at a facility).

In some aspects, any or all of the set of models and/or algorithms can predict the amount of time in which a resource in the environment will be in use, such as, but not limited to, based on contextual data. The set of models and/or algorithms can also predict missed appointments and offer suggestions related to overbooking certain time blocks. In addition, the set of models and/or algorithms can predict the duration in which various resources are used, such as the amount of time needed to capture and analyze captured images, using various optimization tools. For a pre-defined time period (e.g., a workday), the set of models and/or algorithms can predict delays and excess resource utilization over a defined baseline based on real-time updates (e.g., based on the actual end time of a previous appointment, based on an new appointment request, based on a newly acquired scan, etc.). Based on these predicted delays and predicted excess resource utilization, aspects of the present disclosure may thus dynamically, and in real-time, reallocate resources to minimize cascading impacts on subsequent resource utilization in the environment. For example, the set of models and/or algorithms can modify existing time blocks (e.g., by defining a new start time or extending or reducing the duration of a time block) or create new time blocks based on the prediction of future resource utilization. These modifications or creation of new time blocks can optionally include and/or be implemented by transmitting scheduling or rescheduling messaging to one or more health information systems according to a defined message format (e.g., according to messaging formats defined for the Health Level Seven (HL7) standard or other messaging protocols), and/or through the triggering of any other actions (e.g., as described in the method 200 below). New time blocks created by the set of models and/or algorithms may be considered gap opportunities in which unscheduled tasks may be executed in the environment.

In a second set of variants, (e.g., involving worklist generation for a set of radiologists, etc.), additional or alternative to the first, the resource allocation generated by these machine learning models may include an actual and/or predicted set of cases (e.g., arranged in an ordered fashion, arranged in an ordered fashion with predicted cases ordered last, arranged in a non-ordered fashion, etc.) assigned to each of the set of radiologists, wherein the cases assigned to the radiologists are optimized relative to any number of parameters (e.g., as described above).

Additionally or alternatively, the resource allocation can be used to produce any suitable outputs in conjunction with any suitable use cases.

3.22 Set of Regression-Based Models 122a

The set of models and/or algorithms can optionally include one or more regression-based models 122a, such as, but not limited to, a set of regression-based neural networks.

Figure 3:
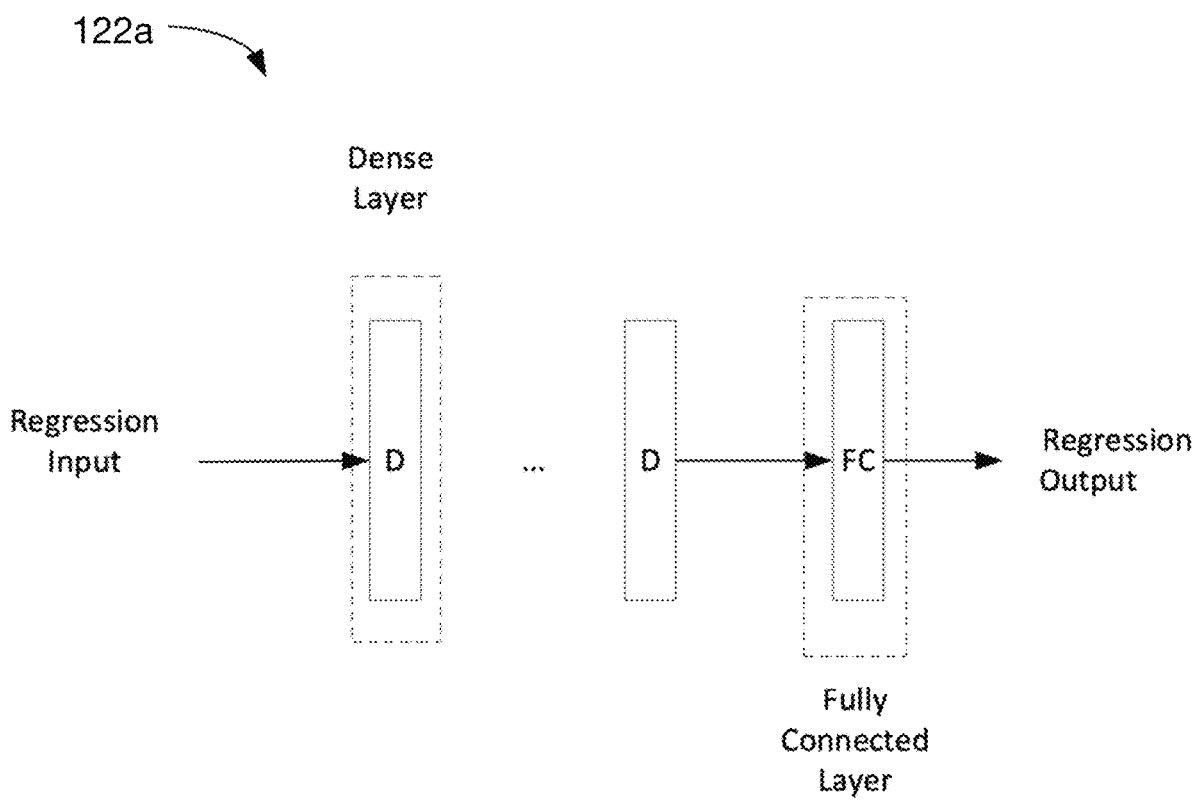
FIG. 3 illustrates an example model for regression in the decision-making subsystem used in optimizing resource allocation.

FIG. 3 depicts an example model for regression used in optimizing resource allocation. Certain aspects herein utilize a machine learning model for solving regression problems during optimizing resource allocation. The regression based model preferably includes a neural network, but can additionally or alternatively include any other trained model (e.g., machine learning model) for solving regression problems. For instance, models other than a neural network could be similarly used, using the same or similar inputs and producing the same or similar outputs as discussed herein.

The regression-based model can take a regression input and generate, based on the regression input, a regression output. The regression output can include a vector of numerical values or any suitable output in any suitable format (e.g., non-binary output, etc.).

The regression-based model can optionally include one or more dense layer layers, such as a dense layer as shown in FIG. 3. In some examples, the neural network includes a plurality of successive dense layers. A dense layer can include one or more output neurons. In preferred examples, any (or all) dense layers can function to learn the linear correlation between its output neurons and inputs to the neurons. In a specific example, a dense layer is implemented as an object or an instance of a standard implementation class, such as PyTorch torch.nn.Linear, TensorFlow tf.keras.layers.Dense, or the like. Additionally or alternatively, any or all dense layers can be otherwise suitably configured.

In some examples, any or all of the dense layers can include an activation function, which can function to help introduce nonlinearity into the regression-based model or perform any other suitable functions. In specific examples, the activation function includes a function applied element-wise to the output of a layer. For instance, the activation function can be a Rectified Linear Unit (ReLU) function, a leaky-ReLU function, or the like. Additionally or alternatively, the activation function and/or the regression-based model can be otherwise suitably configured.

Additionally or alternatively, the regression-based model can include one or more recurrent layers, which includes and functions to provide internal memory. The memory, for instance, can be updated any time there is a new input (e.g., to the model). The output is computed using both the current input and the internal memory. As a result, a recurrent layer can be capable of learning sequential relationship in its inputs. The recurrent layer can additionally or alternatively function to smooth the outputs and reduce noise in predictions.

In some examples, a dense layer in a regression-based neural network, such as one of the dense layers as shown in FIG. 3, can be replaced by a recurrent layer. In some examples, the neural network is a recurrent neural network including a majority of recurrent layers.

The regression-based model can optionally include one or more fully connected layers, such as the fully connected layer shown in FIGS. 3 and/or 4. The fully connected layer can have one or more output neurons. In preferred examples, any or all of the fully connected layers can include all connection weights between its output neurons and the inputs to the neurons, which functions to enable a change in an input to affect all outputs in the fully connected layer. Alternatively, an input can affect a subset of outputs or affect no outputs. The fully connected layer preferably does not apply any activation function on its outputs, but can alternatively be otherwise configured. In some examples, the fully connected layer is implemented as an object or an instance of a standard implementation class, such as PyTorch torch.nn.Linear, TensorFlow tf.keras.layers.Dense, or the like. Additionally or alternatively, the fully connected layer can be otherwise suitably configured.

A final fully connected layer in the regression-based model can determine (e.g., set, define, etc.) the size of the regression output with the number of output neurons. In an example, if the final fully connected layer in a neural network has only one output neuron, the neural network outputs a single numerical value (e.g., a vector of size 1) as the regression output. In another example, if the final fully connected layer in neural network has N output neurons, with integer N greater than 1, the neural network outputs a vector of size N (e.g., including N numerical values) as the regression output. Additionally or alternatively, the neural network and/or fully connected layer can be otherwise suitably configured.

Additionally or alternatively, the set of models can include any other suitable models.

3.23 Set of Classification-Based Models 122b

The set of models and/or algorithms can optionally additionally or alternatively include one or more classification-based models (e.g., as described below), such as, but not limited to, a set of trained classifiers (e.g., classification-based neural network).

Figure 4:
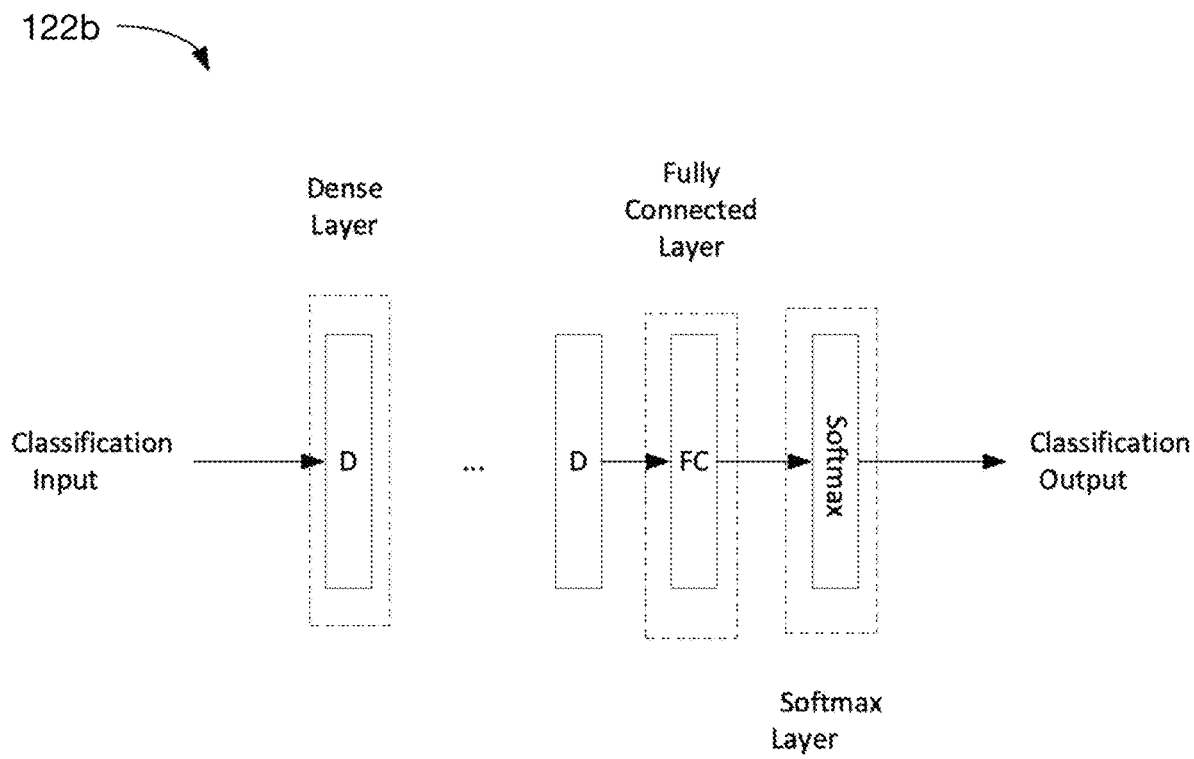
FIG. 4 illustrates an example model for classification in the decision-making subsystem used in optimizing resource allocation.

FIG. 4 depicts an example model for solving classification problems used in optimizing resource allocation. Certain aspects herein utilize one or more machine learning models for solving classification problems during optimizing resource allocation. A neural network is just one example of a machine learning model that can be used for solving classification problems during. However, it should be noted that other models could also be similarly used, using the same or similar inputs and producing the same or similar outputs as discussed herein.

The classification-based model can take one or more classification inputs and generate, based on the classification inputs, a classification output. The classification output(s) can include a numerical value (e.g., binary value of 0 or 1) indicating a pre-defined class corresponding to the classification input(s). The classification output is preferably a binary output (e.g., corresponding to two predetermined classes), but can alternatively correspond to more than two predetermined (e.g., pre-defined) classes, and/or the classification-based model can produce any other number of possible types of outputs.

The classification-based model can include one or more dense layer layers, such as that shown in FIG. 4. In some examples, the classification-based model is a neural network including a plurality of successive dense layers, which can be the same or similar to those shown in FIG. 4, or otherwise suitably configured.

In some examples, the classification-based model includes one or more recurrent layers. In some examples, for instance, a dense layer in a neural network, such as that shown in FIG. 4, can be replaced by a recurrent layer. In some examples, the classification-based model is a recurrent neural network including a majority of recurrent layers.

The classification-based model can include one or more fully connected layers, such as the fully connected layer shown in FIG. 4. The fully connected layer(s) can be the same as or similar to those shown in FIGS. 3 and/or 4. The number of output neurons of the final fully connected layer in the classification-based model is preferably the same as the number of pre-defined classes, but can additionally or alternatively be otherwise defined and/or configured.

The classification-based model can optionally include a softmax layer (e.g., as shown in FIG. 4), which functions to apply a softmax function element-wise to the outputs of the previous layer. If present, the softmax layer preferably follows the final fully connected layer described above, but can alternatively be otherwise suitably arranged. The softmax layer further preferably applies a softmax function or the like (e.g., a sigmoid function, a log softmax function, or the like) to output a vector of likelihood values representing a probability measure—for instance, in some examples, the softmax layer applies the softmax function to the outputs of the previous layer, and outputs a vector of probabilities. In a particular specific example, a log softmax function can be used in place of the softmax function of the softmax layer, where the output from the softmax layer is a vector of log likelihoods. Additionally or alternatively, the classification-based model can be otherwise suitably configured.

The classification-based model preferably outputs one or more classification outputs. In some examples, the classification output is a vector of likelihood values from the softmax layer. In additional or alternative examples, an argmax function can be applied to the vector of likelihood values to find the argument (e.g., the class) with the maximum likelihood value, and the classification output is the argument or a one-hot encoding representation of the argument. Additionally or alternatively, the classification-based model can produce any other outputs in any suitable ways.

Additionally or alternatively, the classification-based model(s) can be otherwise suitably configured.

Additionally or alternatively, the set of models and/or algorithms can include any other suitable types of models (e.g., model architectures) and/or algorithms. For instance, any or all of the set of models and/or algorithms can utilize one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each model can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial least squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each model and/or algorithm can additionally or alternatively be a: probabilistic module, heuristic module, deterministic module, or be any other suitable module leveraging any other suitable computation method, machine learning method, or combination thereof.

Any or all models can be validated, verified, reinforced, calibrated, or otherwise updated based on newly received, up-to-date measurements; past measurements recorded during the operating session; historic measurements recorded during past operating sessions; or be updated based on any other suitable data. Each model can be run or updated: once; at a predetermined frequency; every time the method is performed; every time new data (e.g., appointment end time, actual appointment duration, etc.) and/or an unanticipated measurement value is received; or at any other suitable frequency. The set of models can be run or updated concurrently with one or more other modules, serially, at varying frequencies, or at any other suitable time. Each model can be validated, verified, reinforced, calibrated, or otherwise updated based on newly received, up-to-date data; past data or be updated based on any other suitable data. Each module can be run or updated: in response to determination of an actual result differing from an expected result; or at any other suitable frequency.

3.24 Decision-Making Subsystem Variants

Figure 5A:
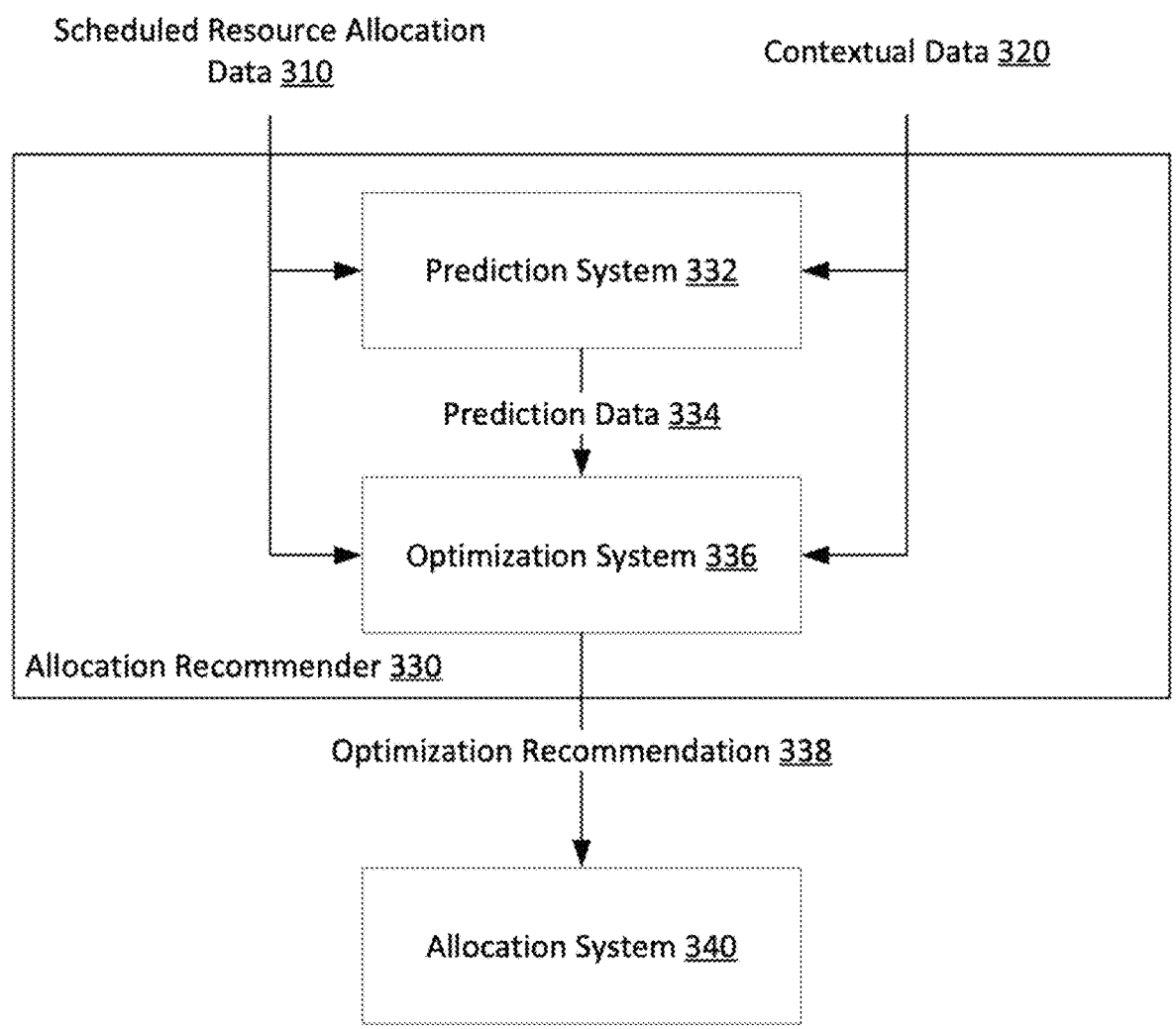
FIGS. 5A and 5B illustrate example resource allocation optimization systems.

FIG. 5A illustrates a decision-making subsystem including and/or configured as an allocation optimization subsystem 300 used in optimizing resource allocation. In particular, the example allocation optimization system 300 can be used in a computing environment. While the foregoing describes specific types of machine learning models that can be used to optimize resource allocation, it should be noted that other models could also be similarly used, using the same or similar inputs and producing the same or similar outputs as discussed herein.

The decision-making subsystem receives a set of inputs (e.g., as described in S210), where the set of inputs can include, but is not limited to, any or all of: data associated with a set of appointments (e.g., a scan type performed during the appointment, times that predetermined appointments have been scheduled for, image data collected during the appointment, etc.); contextual data (e.g., patient data, user data, historical data, facility data, environmental data, etc.); and/or any other data or combination of data.

In a first set of variants, for instance, the decision-making subsystem 300 can take as inputs scheduled resource allocation data 310 (e.g., information associated with a set of scheduled appointments, etc.) and contextual data 320 associated with the scheduled resource allocation data 310, and optimize resource allocation based on the inputs. For example as discussed herein, allocation optimization system 300 may be configured to optimize any or all of: the scheduling of patient procedures, such as imaging procedures (MRI scans, CT scans, X-rays, etc.) performed on patients; the scheduling of user tasks (e.g., which scans a technologist is running, which cases a radiologist is analyzing, etc.); and/or any other tasks or time blocks.

In a second set of variants, the decision-making subsystem can take as inputs medical data in the form of a set of cases and/or studies (e.g., imaging studies) to be analyzed as well as contextual data associated with a set of individuals (e.g., radiologists) performing at least a portion of the analysis of the set of cases and/or studies, such that the decision-making subsystem can optimally assign a workload of cases to each radiologist based on features of the cases and contextual data associated with the radiologists.

The scheduled resource allocation data 310 preferably includes temporal data associated with a set of appointment slots, such as any or all of: a sequence of scheduled time blocks to utilize one or more resources (e.g., device resources such as a scanner time slot, healthcare professional time in meeting with the patient and/or processing the medical data, processing time in a computing environment to process the medical data, etc.), where the temporal information can include and/or define any or all of: a start time, a duration, an end time, a date of the time block, and/or any other information. Additionally or alternatively, the scheduled resource allocation data can include non-temporal data, such as, but not limited to: location data (e.g., facility identifier associated with the procedure), procedure data (e.g., required equipment for the procedure), healthcare professional data (e.g., which healthcare professionals will be involved in and/or required for the procedure), and/or any other data.

The one or more resources can include any or all of: a first set of resources, such as device resources (e.g., MRI scanners); a second set of resources, such as computational resources (e.g., analytical tools or personnel capable of performing analysis); a third set of resources such as healthcare professional time; and/or any other resources. In some aspects, scheduled resource allocation data 310 is only associated with the first set of resources, such as device resources. Details regarding scheduled resource allocation data 310 are discussed in further detail with respect to FIGS. 7-12.

The decision-making subsystem can additionally or alternatively receive contextual data 320, which can include information for one or more users (e.g., patients, healthcare professionals such as radiologists and/or physicians and/or technologists, etc.).

In some variants, for instance, each of a set or subset of patients (e.g., all patients associated with a prior appointment/procedure, all patients associated with a prior appointment/procedure at that facility, all patients associated with data in a medical record database, etc.) is associated with contextual data, where the contextual data can be utilized in optimizing the scheduling of this set or subset of patients, a different (e.g., distinct) set or subset of patients, a set of healthcare professionals (e.g., radiologists, physicians, technologists, etc.) associated with treatment of any patients, and/or any other individuals.

In some examples, each of the plurality of users can have a scheduled time block in the scheduled resource allocation data 310. For example, contextual data 320 can include information for each patient of the plurality of patients. The information for each respective patient or type of patient can include information about historical timeliness, historical deltas between arrival time and scheduled appointment time, evaluation of the conditions of the respective patient or patient type (e.g., a complexity measure from an analysis), or a type of procedure for the respective patient or patient type. This information can be directly gathered, aggregated and/or otherwise used in the calculation of metrics (e.g., average timeliness, etc.), and/or otherwise used. In addition, contextual data 320 can include other information (e.g., predicted information) about a patient or type of patient about whether the patient will be late for an appointment, how late the patient will be for the appointment, and how difficult the imaging process for the patient will be. Furthermore, contextual data 320 can include other information about the scanner and the operator of that scanner as well as the time of the examination.

Additionally or alternatively, environmental contextual data can be utilized to calculate user-related metrics (e.g., temporal metrics associated with predicted lateness to an appointment). For instance, the weather conditions and/or traffic conditions can further exacerbate the lateness of a conventionally tardy patient, make a normally on-time patient late, and/or otherwise shift appointment start times.

Further additionally or alternatively, contextual data in the form of radiologist and/or other user metrics can be processed by the set of models to optimally distribute cases, schedule patient appointments at locations that minimize back-and-forth time of technologists, and/or be otherwise used.

Figure 5B:
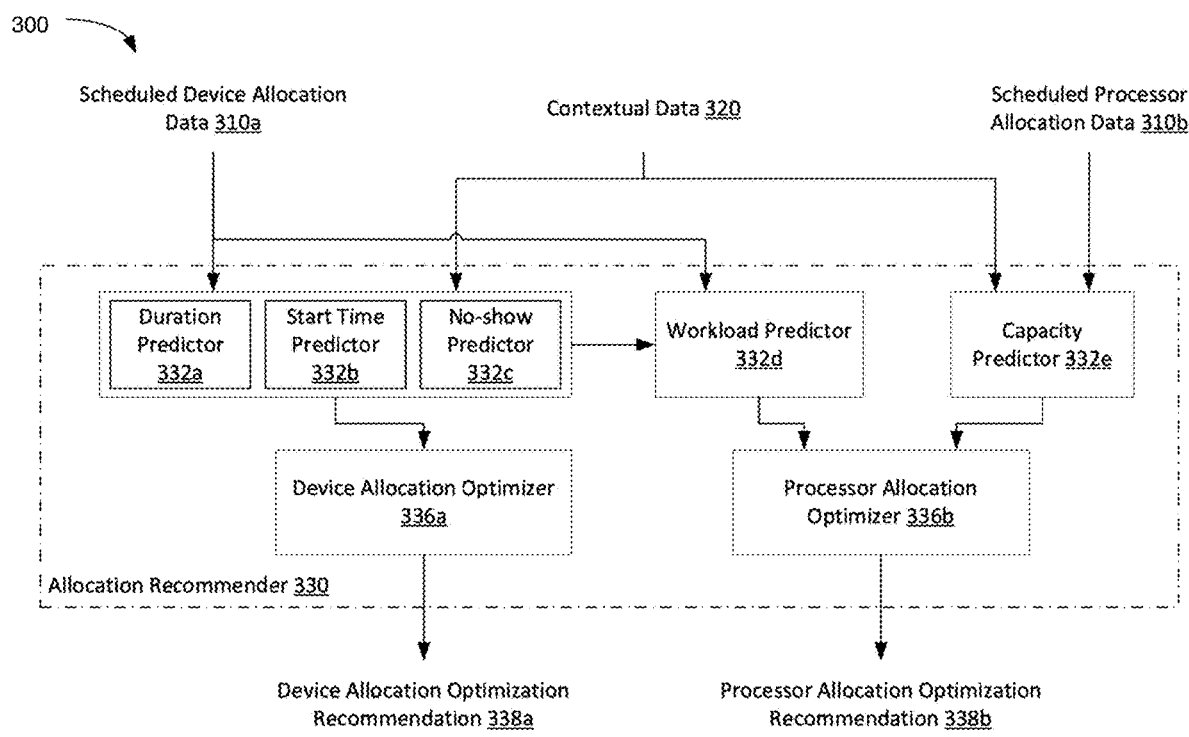

In a preferred set of variants (e.g., as shown in FIGS. 5A-5B), the decision-making subsystem can be organized as a set of one or more prediction sub-models and a set of one or more optimization sub-models. The prediction sub-model(s) can form prediction system 332, which can generate prediction data 334 based on inputs such as, but not limited to, information associated with a set of appointments (equivalently referred to herein as scheduled resource allocation data 310) and contextual data 320. The optimization sub-model(s) can form optimization system 336, which can generate optimization recommendation 338 based on, but not limited to, scheduled resource allocation data 310, contextual data 320, and prediction data 334. Prediction system 332 and optimization system 336 can include one or more machine learning models. In other words, allocation recommender 330 can be a cascading machine model, an ensemble of machine learning models, and/or any other number of models organized (e.g., architected) in any suitable configuration.

Additionally or alternatively, the decision-making subsystem can be otherwise suitably categorized and/or arranged.

The prediction system 332 (or any other model or combination of models in the decision-making subsystem) preferably receives scheduled resource allocation data 310 and contextual data 320 to generate prediction data 334. The prediction system 332 preferably includes one or more machine learning models capable of generating predictions. For example, prediction system 332 can include several distinct machine learning models, where each of the distinct machine learning models can generate different prediction outputs, or an ensemble of machine learning models. In alternative examples, the prediction system 332 can include a single model configured to produce multiple outputs. In yet alternative examples, the prediction system 332 can include a single model configured to produce a single output, 2 models (e.g., 1 classification-based model and 1 regression-based model, etc.), more than 2 models, or any number of models. Additionally or alternatively, the prediction system can be otherwise suitably configured (e.g., with both trained models and untrained [e.g., rule-based] models).

The prediction system 332 is preferably configured, at least in part, to predict a duration of a resource allocation based on contextual data 320. In some examples, information about evaluation about the conditions of the respective patient or the type of procedure for the respective patient in the contextual data 320 can be the inputs to a first (or multiple or single) prediction machine learning model. The resource can include, but is not limited to, a device resource (e.g., scanner such as an MRI machine, etc.), a computational resource, a healthcare professional resource, other resource, or any combination of resources.

A resource allocation preferably includes a time block (e.g., for each patient), which can be defined with respect to a start time, a duration, and/or an end time, to utilize a resource. In some examples, a complexity metric can be determined (e.g., through a pre-processing process as described below) that includes the information about evaluation about the conditions of a patient, a type of procedure for the patient, interpretation of the findings within the imaging exam of the patient in contextual data 320, and/or any other information. In other words, the first prediction machine learning model can predict a duration of resource utilization by a patient (e.g., an imaging for the patient using the resource such as the scan duration of an MRI for the patient) based on any or all of: the complexity of the patient's condition, the imaging protocol, users associated with the scan (e.g., technologist efficiency), environmental conditions, historical scan durations for that patient and/or that scanner and/or that technologist, device resource information (e.g., availability of an MRI machine, imaging time [e.g., average imaging time] associated with a particular scanner, predicted scan time from an algorithm operating at the scanner, etc.), and/or any other information.

The first prediction machine learning model can include a machine learning model capable of solving regression problems. For example, the first prediction machine learning model can include a regression model or a neural network, such as a neural network described in FIG. 3. In a particular example, the first prediction machine learning model can include a transformer model, which can have the benefit of enabling the learning of context (e.g., meaning) by tracking relationships between data occurring sequentially (e.g., words in a sentence). In another example, the first prediction machine learning model can include a recurrent neural network (RNN) (e.g., as described in FIG. 3). The recurrent neural network can be a long short-term memory (LSTM) or a gated recurrent unit (GRU) model. Additionally or alternatively, the model can be of any other type.

Prediction system 332 can include a second prediction machine learning model used to predict missed appointments and use that prediction to overbook appointment slots (e.g., as described below), based on at least the contextual data 320. For example, appointments or appointment slots can be represented as time blocks. In some examples, the historical timeliness of a patient or patient type in contextual data 320 can be input to the second prediction machine learning model. In particular, the historical timeliness of a patient or patient type can indicate for each historical appointment of the patient, whether the patient missed the appointment. Additionally, if an appointment slot is booked by two or more distinct patients, the second prediction machine learning model can receive information about historical timeliness of each of the distinct patients booking the same appointment slot. In other words, the second prediction machine learning model can determine an appointment slot will be missed, overbooked, or neither missed nor overbooked (e.g., as the default), based on the historical timeliness of patients or patient types.

The second prediction machine learning model can include a machine learning model capable of solving classification problems. For example, the second prediction machine learning model can include logistic regression, decision tree, random forest, gradient-boosted tree, support vector machine K-nearest neighbor, or naïve Bayes. For example, the second prediction machine learning model can include a pipeline (e.g., a cascaded) or ensemble of machine learning models. Additionally, the second prediction machine learning model can include a neural network, such as a classification-based model 122b as described in FIG. 4. In particular, the second prediction machine learning model can include a recurrent neural network (e.g., as shown in FIG. 4). The recurrent neural network can be an LSTM model and/or any other suitable model or model having any suitable architecture. Additionally or alternatively, the second prediction machine learning model can be otherwise configured.

Prediction system 332 can include a third prediction machine learning model used to predict a delay duration for at least one patient based on the contextual data 320. For example, historical deltas between arrival time and scheduled appointment time in contextual data 320, or in other words, how late the patient or patient type was for past appointments, can be the input to the third prediction machine learning model. The third prediction machine learning model can predict how late the patient will be for an appointment based on how late the patient or type of patient was for appointments in the past.

The third prediction machine learning model can include a machine learning model capable of solving regression problems. For example, the third prediction machine learning model can include a regression model or a neural network, such as a neural network as described in FIG. 1. In particular, the third prediction machine learning model can include a recurrent neural network, as described in FIG. 1. The recurrent neural network can be an LSTM model. Additionally or alternatively, the third prediction machine learning model can be otherwise configured.

Prediction system 332 can include a fourth prediction machine learning model used to predict a duration over a threshold time that resources will be used, based on scheduled resource allocation data 310, the durations of the resource allocation from the first prediction machine learning model, and the delay durations from the third prediction machine learning model. For example, the duration over a threshold time that resources will be used can be an overtime of resources. In particular, the threshold time can be a scheduled end time for all resource usage, such as a scheduled end time of the workday (e.g., 6 P.M./1800 hr).

The fourth prediction machine learning model can include a machine learning model capable of solving regression problems. For example, the fourth prediction machine learning model can include a regression model or a neural network, such as a neural network as described in FIG. 3. In particular, the fourth prediction machine learning model can include a recurrent neural network, as described in FIG. 3. The recurrent neural network can be an LSTM model. Additionally or alternatively, the fourth prediction machine learning model can be otherwise configured.

Prediction system 332 can include a fifth prediction machine learning model used to predict idle resource allocations that an unscheduled task can utilize based on scheduled resource allocation data 310, the durations of the resource allocation from the first prediction machine learning model, and the delay durations from the third prediction machine learning model. For example, new time blocks can be created and designated as gap opportunities. In some examples, the gap opportunity can be utilized if the gap opportunity meets a threshold duration. For example, a gap opportunity can be used for new scans, which is known as scan acquisition.

The fifth prediction machine learning model can include a machine learning model capable of solving optimization problems. The outputs of prediction system 332 can be aggregated into prediction data 334. For example, prediction data 334 can include the durations of the resource allocation from the first prediction machine learning model, predicted missed appointments and overbook appointment slots from the second prediction machine learning model, the delay durations from the third prediction machine learning model, the durations over a threshold time that resources will be used from the fourth prediction machine learning model, and idle resource allocations that an unscheduled task can utilize from the fifth prediction machine learning model. Additionally or alternatively, the fifth prediction machine learning model can be otherwise configured.

Additionally or alternatively, the prediction subsystem can combine any or all of the above models into a single model and/or can be otherwise suitably configured.

The decision-making subsystem 110 can optionally additionally or alternatively include an optimization system 336, which can take as inputs, any or all of: scheduled resource allocation data 310, contextual data 320, prediction data 334, and/or any other data. Given that resource allocation is dynamic as patients might be late for appointments, appointments might end early, and unscheduled patients can enter and resources need to be reallocated to image unscheduled patients. The optimization system (and/or the prediction system) can optionally be run iteratively (e.g., as new contextual data is received, as new appointment information is received, as previous appointments are completed, at a predetermined frequency, etc.) such that the schedule(s) are dynamically maintained. Optimization system 336 can include an optimization machine learning model and/or multiple optimization machine learning models. For example, optimization system 336 can be a machine learning model or a recommender system capable of handling dynamic or sequential inputs. Optimization system 336 can recognize a current state and perform actions, and the actions of the optimization system 336 can influence the next state. A state can be defined with respect to scheduled resource allocation data 310 and prediction data 334. For example, a state can be a time block during which a resource is used to treat an upcoming scheduled patient. In addition, the state can indicate the duration of the resource allocation, whether another patient booked an appointment to use the resource during the time block, whether the time block will be a missed appointment or overbooked appointment, the delay duration of the upcoming scheduled patient, and whether the time block includes idle resource allocations that an unscheduled task can utilize, based on prediction data 334.

Accordingly, the actions of optimization system 336 for the current state can include admitting one of the scheduled patients, admitting an unscheduled patient, and admitting no patient. Additionally, the actions of optimization system 336 can include changing the start time of the time block or changing the end time of the time block. In some examples, optimization system 336 reaches a terminal state when there are no more patients waiting to use the resources. The set of actions generated by optimization system 336 can be used to generate an optimized allocation of the first set of resources.

In additional or alternative variants, the optimization system can be used to assign cases to particular users (e.g., radiologists, technologists, etc.), distribute cases among multiple users (e.g., radiologists), select a set of cases that when aggregated are an appropriate mix for each radiologist (e.g., in comparison with contextual data associated with the radiologist, in comparison with the caseload of other radiologists, etc.), and/or otherwise produce a set of outputs.

In some aspects, for instance, allocation optimization system 300 can generate an optimized allocation of the second set of resources in the computing environment. In some examples, generating the optimized allocation of the second set of resources is based on generating the optimized allocation of the first set of resources. In some examples, the optimized allocation of the second set of resources is generated in combination with the first set of resources. For example, the first set of resources represents the device resources whereas the second set of resources represents the computational resources, time blocks allocated to the scheduled second set of resources can be combined with (e.g., appended to) time blocks allocated to the scheduled first set of resources. The combined time blocks can be optimized by allocation optimization system 300 to generate optimized allocation of the first set of resources and the second set of resources. In some examples, the optimized allocation of the second set of resources is generated using stepwise optimization and global optimization methods. In some aspects, the machine learning models may output an allocation of resources including starting times for each of the scheduled time blocks in the input scheduled resource allocation data and a predicted duration for each of these time blocks. Various techniques may be used to further optimize resource allocation. For example, gaps between an ending time of a first time block and the beginning time of a second time block may be analyzed to determine whether it is feasible to move such a gap to another time (e.g., based on the difference between an original beginning time for the second time block and a new beginning time for the second time block) to minimize an amount of time by which a scheduled time block is shifted. Generally, because it may not be desirable to shift a time block by more than a threshold amount of time (which may be defined a priori or may be a user-defined value), time blocks may be shifted if the beginning time changes by less than the threshold amount of time and may remain the same if the beginning time changes by more than the threshold amount of time. In some aspects, if aggregated gaps result in an unallocated block of time that allows for an unscheduled use of resources in the environment, the unallocated block may be reserved for such unscheduled use or may be used to move another scheduled time block to an earlier execution time if desired. Overall, the allocation of resources generally attempts to generate the maximum number and/or size of open slots while minimizing the number and/or size of modifications to the original schedule of time blocks.

In some aspects, the machine learning models may also or alternatively be used to suggest adjustments to scheduled patient appointments to further optimize the allocation of time resources. Generally, these suggested adjustments may include suggestions to adjust a starting time for an appointment to an earlier or later time slot based on the availability of time windows in which an appointment can be scheduled, including time windows generated from segments of time that exist due to some procedures having a projected completion time that is less than an a priori defined time block for a procedure. In some aspects, the suggested adjustments may include adjustments that cause the start time for a procedure to be moved by less than a threshold amount of time. The threshold amount of time may be defined a priori as a global variable, may be defined for each patient or type of patient, etc.

The machine learning models may predict a likelihood of a scheduled time block being unused or otherwise canceled. If a time block has a likelihood of cancellation or otherwise being unused that exceeds a threshold value, the time block may be considered a candidate for overbooking. In doing so, the time block may be marked as a candidate time block that allows for an unscheduled use of resources in the environment. If a conflict arises between the scheduled time block and unscheduled use of resources in the environment, a new allocation may be input into the machine learning models discussed above to obtain a new optimized resource allocation that allows for the resources in the environment to be allocated to both the task associated with the scheduled time block and the unscheduled use.

The optimized allocation of the first set of resources in the computing environment and the second set of resources in the computing environment can be output as optimization recommendation 338. In some examples, optimization recommendation 338 is dynamic. For example, optimization system 336 can output a set of actions for one state at a time. Optimization recommendation 338 can be sent to allocation system 340. Allocation system 340 can generate commands to execute optimization recommendation 338.

In general, allocation optimization system 300 can increase the number of resource utilization during a predefined time period (e.g., a workday), reduce patient wait time, reduce resource overtime, and reduce delta between the original start time allocated to a resource and optimized start time allocated to the resource. Details about methods to achieve the benefits brought by the allocation optimization system 300 can be found with respect to FIG. 6 below.

In some aspects, allocation optimization system 300 can also or alternatively be used to optimize the scheduling of compute resources (e.g., staff) for performing scheduled (and potentially unscheduled) procedures and processing outputs generated during these procedures. For example, in an environment in which resources are scheduled to perform imaging studies on patients, the scheduling of these resources may include scheduling personnel to operate the imaging devices and process captured images for the patients for which imaging studies have been scheduled. In such a case, scheduled resource allocation data 310 may include a sequence of scheduled time blocks in which various tasks and utilization of one or more resources in a computing environment are scheduled as well as information about a current group of personnel (or other processing resources) assigned to perform the scheduled tasks. The contextual data 320 may include information about the scheduled studies associated with each time block and capability information about the personnel who can be scheduled to operate the imaging devices and process the captured images. Generally, the information about the scheduled studies associated with each time block may include a complexity metric (e.g., as determined through preprocessing in the method 200) indicating the complexity of a study or procedure (e.g., a relative value unit [RVU] defined for the amount of work involved in a procedure, which may be an external defined measurement that is used to determine the cost (e.g., in time, resources, financial cost, etc.) of a procedure (e.g., scheduled procedure, predicted procedure, etc.) such that more complex procedures incur higher costs and less complex procedures incur lower costs). The contextual information about the personnel who can be scheduled to operate the imaging devices and process captured images for the patients for which imaging studies have been scheduled may, in some aspects, include information about an amount of experience each person has (which may be used as a proxy measure for efficiency or throughput), historical utilization and efficiency information, and other information that can be used as an indication of an amount of work that a person can perform during a given time period.

In some aspects, a complexity metric indicating the complexity of a study or procedure may be generated based on an analysis of previous times similar studies or procedures have been performed. To do so, various techniques can be used to parse complexity information from various inputs. For example, natural language processing techniques can be applied to narratives associated with previous studies of a given type to identify specific concepts, such as specific clinical concepts or subject matter concepts, associated with specific complexity measures (e.g., a time measure, a computational expense measure (in terms of operations performed over a given period of time), etc.). In some aspects, the complexity of a study may be determined based on the complexity of prior similar studies (e.g., as determined based on the processing and/or analysis of previous reports for similar or same pathologies and/or patients, using report length as a proxy for complexity, etc.). In still further aspects, the complexity of a study may be determined based on a difference, or delta, between a template defined for a generic task and the content of a report generated for a study. Of course, it should be recognized that other techniques can be used to determine the complexity of a study or procedure, and the resulting determination of the complexity of a study or procedure can be used as contextual information provided as input into a resource allocation optimization system.

The complexity metrics can additionally or alternatively be used to determine which cases are assigned and/or how to determine a distribution of cases assigned to each radiologist (e.g., as described below). In some variants, for instance, the cases assigned to a particular radiologist can be collectively chosen to have any or all of: an average complexity below a first threshold and/or above a second threshold (e.g., based on the radiologist's experience level, based on the radiologist's efficiency level, ensuring that experienced radiologists have at least a portion of low complexity cases, etc.); all complexities below a predetermined threshold; all complexities above a predetermined threshold; and/or any other distribution of complexities.

Prediction system 332 can use the schedule resource allocation data 310 including the scheduled procedures for the plurality of patients and the contextual data 320 including complexity information associated with the scheduled procedures and capability information about the personnel who can be scheduled to operate the imaging devices and process the captured images as an input to generate prediction data 334 including a predicted an amount of work to be performed over a time period (e.g., during a work day or a defined shift in which personnel can be assigned to perform various tasks). In this example, prediction system 332 and optimization system 336 may be configured to optimize throughput, unlike in the example discussed above in which an appointment schedule is generated to optimize resource utilization and minimize the amount of time in which compute resources are idle. Generally, prediction system 332 can also generate, based on the scheduled resource allocation data 310 and contextual data 320, one or more candidate sets of personnel that can provide sufficient resources to perform the amount of work involved in performing the scheduled procedures.

Based on the predicted amount of work and the candidate set of personnel generated by prediction system 332, optimization system 336 can attempt to schedule personnel in the candidate set of personnel to perform the scheduled procedures. Generally, optimization system 336 may be configured to generate assignments of personnel or other processing resources to minimize an amount of idle time for the personnel scheduled to perform the scheduled procedures, minimize an elapsed time between data capture and data processing, and take into account other relevant considerations in scheduling. For example, the optimization system may be configured (trained) to assign personnel or other resources to different procedures based on credentialing information or capability information associated with each person who can be scheduled to work in the processing environment. Generally, optimization system 336 may be blocked from assigning personnel with insufficient credentials to perform various procedures, which may provide a limit on the universe of optimized schedules that can be generated by allocation recommender 330. In another example, the capability information associated with each person who can be scheduled to work in the processing environment can be used, in conjunction with the complexity information associated with the scheduled procedures, to determine which persons or processing resources are to be assigned to perform various procedures. For example, given a timing constraint such as a target amount of time elapsed between completion of image capture procedures on a patient and generating a diagnosis for that patient, the complexity information associated with the procedure can be used to determine how to assign different personnel for processing these images. More complex procedures may be assigned to personnel with more experience or a history of performing these complex procedures more efficiently, while less complex procedures may be assigned to personnel with less experience.

In some aspects, optimization system 336 can attempt to distribute work across multiple people (or other processing resources) in a fair manner. In doing so, optimization system 336 can be configured to assign each person (or processing resource) tasks of varying complexity so that no single person is assigned to perform tasks at a single or small number of complexity levels. Further, optimization system 336 can be configured to distribute work to minimize a number of people who are assigned tasks that are projected to extend beyond the end of a defined block of time in which these people are scheduled to work. In some aspects, when a threshold number of people are assigned to work beyond the end of a defined block of time, optimization system 336 may also recommend that additional personnel (or other processing resources) be assigned to perform tasks so that personnel already assigned to perform various procedures or portions thereof are not scheduled to perform such procedures beyond the end of the defined block of time. The recommendations of personnel to perform various tasks, including the recommendations of additional personnel to assign beyond the current group of personnel provided as input into prediction system 332, may also take into account personnel-specific preferences to determine who is eligible to be scheduled to work within any given time block, such as preferences on days of the week during which these personnel will work, vacation and time-off preferences, time preferences, and the like.

In some aspects, allocation system 300A can optimize device and/or processor optimization on a per-location basis or on a cross-location basis. In examples in which allocation system 300A optimizes device and/or processor optimization on a cross-location basis, additional contextual constraints may influence how scheduled resource utilization and processor utilization is optimized. For example, geographic distance between different locations over which scheduled resource utilization and processor utilization may be considered in moving procedures between different locations. Generally, for resources located in the same or substantially similar locations, such as resources located in different portions of a same campus, procedures can be moved between locations without geographical constraints. For resources located in different locations, the distance between these locations, as well as the location of the patients for which procedures are to be performed, may be considered in determining whether a procedure is eligible to be moved from one location to another location. Generally, allocation system 300 may be trained to minimize location changes and may be trained to minimize changes in the distance over which a patient is to travel in order for the procedure to be performed. In some aspects, other constraints may further influence how scheduling procedures are optimized. For example, procedures which are designated as non-movable for any number of reasons (e.g., patient condition, physician privileges, etc.) may not be moved from one location to another location, which may limit the universe of procedures which can be moved from one location to another.

FIG. 5B illustrates an example allocation system 300 in which device utilization and processor (personnel) allocation are jointly optimized. As illustrated, allocation recommender 330 includes a plurality of predictors 332a-332c which are configured to use scheduled device allocation data 310a and contextual data 320 to generate various predictions with respect to the utilization of various devices in a computing environment (e.g., imaging devices, such as MRI scanners, CT scanners, X-ray machines, etc. in a medical imaging environment), such as timing information, and no-show information (e.g., which scheduled procedures are likely not to happen because the patient on which these procedures are to be performed will not show up for the appointment). Similarly, predictors 332d-332e may be configured to use scheduled processor allocation data 310b (e.g., personnel scheduled to perform the procedures associated with scheduled device allocation data 310a), contextual data 320 about the processors (personnel), and recommended device scheduling generated by predictors 332a-332c to generate various predictions with respect to processing resources that can perform the tasks associated with the recommended device scheduling.

In some variants, the workload predictor 332d functions to predict a volume of cases that will need to be and/or will be available to be analyzed during a predetermined time period by the set of radiologists. Additionally or alternatively, the workload predictor can function to predict a number of appointments and/or appointment tasks (e.g., scans) to be performed during the time period, where the predicted appointments are used to determine the predicted number of cases. The workload predictor preferably includes a set of trained models and/or algorithms (e.g., as described above), such as a set of models that process any or all of the set of inputs (e.g., contextual data associated with the facility, historical trends associated with the facility, etc.) to determine the predicted volume.

Allocation optimization system 300 can take as inputs scheduled device allocation data 310a, scheduled processor allocation data 310b, and contextual data 320 associated with the scheduled device and processor allocation data 310a-b, and generates device allocation optimization recommendation 338a and processor allocation optimization recommendation 338b based on the inputs. Scheduled device allocation data 310a and scheduled processor allocation data 310b can be examples of, or parts of, respectively, scheduled resource allocation data 310 shown in FIG. 5A, whereas device allocation optimization recommendation 338a and processor allocation optimization recommendation 338b can be examples of, or parts of, respectively, optimization recommendation 338 shown in FIG. 5A. Although illustrated as one contiguous block, contextual data 320 can be separated into contextual data associated with the scheduled device allocation data 310a and contextual data associated with the scheduled processor allocation data 310b, respectively, and provided as inputs to subsequent predictors and optimizers accordingly.

Scheduled device allocation data 310a and contextual data 320 can be provided as inputs to duration predictor 332a to predict durations of device usage for a plurality of devices. Duration predictor 332a can be a part of prediction system 332. For example, duration predictor 332a can use the first prediction machine learning model discussed with respect to FIG. 5A to predict a duration of a device allocation based on scheduled device allocation data 310a and contextual data 320. Additionally or alternatively, durations of entire appointments can be predicted, and/or any other durations can be determined.

Similarly, scheduled device allocation data 310a and contextual data 320 can be provided as inputs to start time predictor 332b to predict start times of device usage for the plurality of devices (and/or appointment times for a set of appointments). Start time predictor 332b can be a part of prediction system 332. For example, start time predictor 332b can also use the first prediction machine learning model discussed with respect to FIG. 5A to predict a start time of a device allocation based on scheduled device allocation data 310a and contextual data 320.

In addition, scheduled device allocation data 310a and contextual data 320 can be provided as inputs to no-show predictor 332c to predict under-utilization events for devices for the plurality of devices. No-show predictor 332c can be a part of prediction system 332. For example, no-show predictor 332c can use the second prediction machine learning model discussed with respect to FIG. 5A to predict an under-utilization event in a device allocation based on scheduled device allocation data 310a and contextual data 320.

As illustrated, the durations of device usage predicted by duration predictor 332a, the start times of device usage predicted by start time predictor 332b, and the under-utilization events predicted by no-show predictor 332c can be provided as inputs to device allocation optimizer 336a to generate device allocation optimization recommendation 338a. Device allocation optimizer 336a can be a part of optimization system 336. For example, device allocation optimizer 336a can optimize the scheduled device allocation indicated in scheduled device allocation data 310a, as discussed with respect to FIG. 5A, and generates an optimized schedule of device allocation as the device allocation optimization recommendation 338a.

In addition, as illustrated, scheduled device allocation data 310a together with the durations of device usage predicted by duration predictor 332a, the start times of device usage predicted by start time predictor 332b, and the under-utilization events predicted by no-show predictor 332c, can be provided as inputs to workload predictor 332d to predict workload for a plurality of processors. In some examples, part of contextual data 320 (e.g., complexity of tasks) can also be provided as inputs to workload predictor 332d. Workload predictor 332d can be a part of prediction system 332. Workload predictor 332d can use machine learning models to predict the workload. For example, workload predictor 332d can use a regression model or an ensemble of multiple regression models to predict the workload. In an example, workload predictor 332d include a regression model capable of detecting seasonal trends (e.g., Prophet), where the inputs to the regression model include the unknown scheduled cases, predicted additions and/or cancellations for a period of time in the future, weather information, and other contextual data that may influence a scheduled allocation of device resources within a computing environment.

Scheduled processor allocation data 310b and contextual data 320 can be provided as inputs to capacity predictor 332e to predict capacities for the plurality of processors and/or processing entities (e.g., radiologists analyzing cases to generate reports). Capacity predictor 332e can be a part of prediction system 332. Capacity predictor 332e can use machine learning models to predict the capacity. For example, capacity predictor 332e can use a regression model or an ensemble of multiple regression models to predict the capacity for the processors. In an example, capacity predictor 332e predicts the capacity of a processor using a gradient-boosted machine (e.g., LightGBM) based on the scheduled processor allocation data 310b and contextual data 320 (e.g., processing requirement for tasks). In some examples, additionally or alternatively, capacity predicted by capacity predictor 332e include a duration for a processor to complete a task, which can be predicted using additional regression model(s) (e.g., linear regression model, gradient-boosted tree, or gradient-boosted machine).

The workload predicted by workload predictor 332d and the capacity predicted by capacity predictor 332e, can be provided as inputs to processor allocation optimizer 336b to generate processor allocation optimization recommendation 338b. Processor allocation optimizer 336b can be a part of optimization system 336. For example, processor allocation optimizer 336b can optimize the scheduled processor allocation indicated in scheduled processor allocation data 310b, as discussed with respect to FIG. 5A, and generates an optimized schedule of processor allocation as the processor allocation optimization recommendation 338b. In some examples, additionally or alternatively, processor allocation optimizer 336b uses machine learning model(s) different from the machine learning model in optimization system 336 to optimize the scheduled processor allocation. For example, processor allocation optimizer 336b can use a classifier to determine a time period during which an over-capacity event and a later under-capacity event will be likely to happen, and then allocate one or more processors in the later under-capacity event to the over-capacity event, so as to balance the capacity.

Additionally or alternatively, the set of models can be otherwise configured, used to process other inputs, and/or be otherwise suitably implemented.

3.3 Set of Schedules 130

The system 100 can include and/or interface with (e.g., produce) a set of schedules, such as with the set of models and/or algorithms (e.g., as described above). The schedules can be patient schedules, facility schedules, facility personnel schedules (e.g., radiologist worklists, technologist schedule and/or tasks, etc.), and/or any other schedules. The schedules can be any or all of: actual schedules, predicted schedules, historical schedules (e.g., for use as contextual data), and/or any combination. The set of schedules are preferably iteratively and dynamically adjusted during the method 200, but can additionally or alternatively be otherwise configured.

3.4 Set of User Interfaces 140

The system 100 can optionally include and/or interface with a set of user interfaces 140 (equivalently referred to herein as I/O device interfaces), such as any or all of those described above, which can be utilized for any or all of: receiving inputs of the set of inputs from one or more users, providing outputs (e.g., schedules) to one or more users, and/or otherwise interfacing with the system and/or method. The user interfaces can include input devices (e.g., buttons, keyboards, touch interfaces, etc.), output devices (e.g., displays), and/or any other components.

4. Method 200

As shown in FIG. 2, a method 200 for resource optimization includes: receiving a set of inputs S210; and processing the set of inputs and/or contextual data with a set of models to produce a set of schedules S230. Additionally or alternatively, the method 200 can include any or all of: training the set of models S205; pre-processing the set of inputs to supplement the set of contextual data S220; dynamically adjusting the set of schedules S240; triggering a set of actions based on the set of schedules S250; updating the set of models S260; and/or any other processes. Further additionally or alternatively, the method 200 can include and/or interface with any or all of the methods, processes, embodiments, and/or examples as described in any or all of: U.S. application Ser. No. 17/649,213, filed 28 Jan. 2022; U.S. application Ser. No. 16/688,623, filed 19 Nov. 2019, now issued as U.S. Pat. No. 11,610,667; U.S. application Ser. No. 17/020,593, filed 14 Sep. 2020, now issued as U.S. Pat. No. 11,342,055; U.S. application Ser. No. 17/690,751, filed 9 Mar. 2022, now issued as U.S. Pat. No. 11,615,890; and U.S. application Ser. No. 18/215,354, filed 28 Jun. 2023; each of which is incorporated herein in its entirety by this reference.

The method 200 is preferably performed with a system 100 as described above, but can additionally or alternatively be performed with any other suitable system(s) and/or combination of systems.

The method 200 preferably functions to optimize the allocation of a set of resources (e.g., as described above), such as through, but not limited to, any or all of: optimizing a set of schedules, fairly distributing a set of cases to a set of radiologists, and/or otherwise optimizing operations associated with a facility. Additionally or alternatively, the method 200 can function to dynamically and iteratively update the set of schedules and/or otherwise maintain an up-to-date optimization of the set of resources.

4.1 Method: Receiving a Set of Inputs S210

The method 200 includes receiving a set of inputs S210, which functions to collect information with which to optimize the allocation of resources. S210 is preferably performed at least initially in the method 200, but can additionally be performed throughout the method (e.g., continuously, at predetermined intervals, as tasks are performed, etc.) and/or at any other times.

The set of inputs can include, but is not limited to, any or all of: data associated with a set of appointments (e.g., set of tasks, temporal information, scan information, scanner information, etc.) and/or contextual data. The contextual data can include, but is not limited to, any or all of: patient data (e.g., demographic information, medical history, prior set of appointments, etc.); user (e.g., facility personnel) data (e.g., radiologist performance metrics, technologist performance metrics, scheduling/shift information, etc.); historical data (e.g., for patients or other users, for the facility, etc.); facility data (e.g., layout information of scanners, distance between scanners, etc.); environmental data (e.g., weather information, traffic information, etc.); and/or any other inputs.

The set of inputs can be received from (e.g., retrieved from) any or all of: a set of databases, lookup tables, memory, sensors, devices (e.g., scanners), and/or any other information sources.

Additionally or alternatively, the system 100 can include any other components.

The set of inputs is preferably received at the decision-making subsystem but can optionally be received at any other locations and/or components.

4.2 Method: Pre-Processing the Set of Inputs to Supplement the Contextual Data S220

The method 200 can optionally include pre-processing any or all of the set of inputs, which functions to produce additional metrics with which to optimize the allocation of a set of resources. S220 is preferably performed in response to and/or based on any or all iterations of S210, but can additionally or alternatively be performed at any other suitable time(s).

Pre-processing the set of inputs preferably includes calculating a set of complexity metrics (e.g., as described above) associated with each of a set of appointments and/or appointment tasks (e.g., scans), where the appointments can be predetermined (e.g., scheduled), predicted (e.g., with a set of models and/or algorithms), and/or any combination. The set of complexity metrics are preferably determined with one or more of the set of models and/or algorithms but can additionally or alternatively be otherwise suitably calculated (e.g., with a set of rules, based on a set of lookup tables, etc.). Alternatively, the complexity metrics can be predetermined.

Additionally or alternatively, any other metrics can be calculated.

4.3 Method: Processing the Set of Inputs and/or the Contextual Data with the Set of Models to Produce a Set of Schedules S230

The method 200 preferably includes processing the set of inputs and/or the contextual data with the set of models to produce a set of schedules S230, which functions to produce schedules that are configured to optimize an allocation of resources. Additionally or alternatively, any other outputs can be produced in S230.

S230 is preferably performed in response to and/or based on S210 and/or S220, but can additionally or alternatively be performed during S240, in response to S240, in response to S250, multiple times during the method 200, and/or at any other times.

S230 is preferably performed with the decision-making subsystem no (e.g., including an allocation system 300, including an optimization system, etc.) (e.g., as described above), and further preferably with a set of models and/or algorithms 122, but can additionally or alternatively be performed with any other suitable models or tools.

In a first set of variants, S230 includes processing any or all of: initial scheduling information (e.g., a set of predetermined scans that have already been scheduled and their initial temporal information), predicted scheduling information (e.g., based on a predicted volume of cases), and contextual data (e.g., historical information associated with previous timeliness of the patients that have scheduled scans, environmental information associated with the facility, etc.), with the set of models and/or algorithms to determine an initial, optimized schedule, wherein determining the initial, optimized schedule can include, for instance, any or all of: overbooking a subset of appointments (e.g., associated with patients having a high no-show probability, associated with 1 patient having a high lateness likelihood and another patient having a high earliness likelihood, associated with multiple patients having low complexity scans, etc.); shifting the start time of a subset of appointments; adjusting the duration of a subset of appointments (e.g., increasing the duration of high complexity scans, decreasing the duration of low complexity scans, etc.); creating and/or aggregating gaps in the schedule to create new appointment slots (e.g., upon determining that the gaps exceed at least a minimum temporal duration threshold); inserting new appointment requests into the new appointment slots; and/or otherwise creating a schedule at a facility associated with a set of patients.

In a second set of variants, S230 includes processing any or all of: previously completed appointment information (e.g., images from previously completed scans), future scheduled appointment information (e.g., scans that will be performed), predicted scheduled scan information (e.g., based on a predicted volume of scans), and/or contextual data associated with the patients (e.g., patient lateness information, medical history information, etc.), facility (e.g., historical volume trends), scan (e.g., predicted complexity score, actual complexity score, etc.) and/or users performing the processing (e.g., radiologist performance metrics) to distribute the actual and/or predicted tasks (e.g., radiologist review tasks and report generation, technologist scan performance, etc.) among the set of users (e.g., radiologists, technologists, etc.). In examples, the radiologist schedules (e.g., radiologist worklist) are optimized for any or all of: fairly distributing complex cases among multiple radiologists (e.g., ensuring that a radiologist having an experience level above a predetermined threshold is assigned cases having a complexity score below a predetermined threshold, etc.), distributing cases of varying complexity to each radiologist, matching a radiologist experience level and/or expertise level and/or specialty metric(s) with his assigned cases, distributing cases based on an adjusted efficiency metric for a radiologist wherein the adjusted efficiency metric is adjusted relative to his standard efficiency metric (e.g., based on who he is working with that shift and historical information about their collective efficiency, based on other contextual data such as time of day and/or time of year, etc.), and/or otherwise optimally distributed. In other examples, the technologist schedules are optimized for any or all of: minimizing downtime, minimizing the distance the technologist has to travel between scan locations (e.g., which can cause delays), and/or otherwise optimizing the technologist schedules.

In a set of examples, any or all of the following can be considered in determining and/or adjusting the cases distributed to and/or among radiologists: individually distinct procedure speeds, distinct abilities and speeds for each different type of procedure, varying speed depending on time of day and day of the week, varying speed depending on the specific order in which they review the procedures, and/or any other metrics, such as, but not limited to, any or all of those described in U.S. application Ser. No. 17/649,213, filed 28 Jan. 2022. In preferred examples, the method enables incorporating any or all of these metrics into the forecasting model inputs and optionally refining of the outputs, to enable, for instance, any or all of: determining which specific procedures to assign to each radiologist in what specific order; determining which subset of procedures to assign versus allowing the radiologist the ability to select their choice of the other procedures; and/or any other outcomes.

4.4 Method: Dynamically Adjusting the Set of Schedules S240

The method 200 can optionally include dynamically adjusting any or all of the set of schedules S240, which functions to optimize any or all schedules as new information (e.g., new inputs in S210, information from completed appointments, etc.) is received. As such, S240 preferably functions to enable the schedules to continue to be optimized as time progresses (e.g., and patients show up late to appointments, as appointments end earlier or later than expected, etc.). Additionally or alternatively, S240 can function to maximize a number of patients that can be scanned throughout the day, minimize an amount of downtime, and/or otherwise confer any suitable benefits.

S240 is preferably performed continuously during the method 200 and after S230, such as in an iterative fashion. S240 can be triggered according to receipt of new information (e.g., new appointment information), the determination that a scan has ended or has been initiated (e.g., based on facility information, based on inputs received at a user interface, etc.), upon completion of a task, according to a predetermined set of intervals (e.g., at a predetermined frequency), and/or at any other suitable times.

S240 preferably includes repeating an instance of S230 but can additionally or alternatively be performed differently than S230, with other models and/or algorithms, absent of the set of models and/or algorithms, and/or otherwise suitably performed.

In a preferred set of variants, each time a scan is initiated or completed, S230 is re-run to produce an adjusted schedule for the set of patients at the facility.

Additionally or alternatively, the technologist schedule can be updated, the radiologist worklists can be adjusted (e.g., re-ordered, changed to include completed scan information, etc.), and/or any other outputs can be created or adjusted.

4.5 Method: Triggering a Set of Actions Based on the Set of Schedules S250

The method 200 can optionally include triggering a set of actions based on the set of schedules, which can function to execute and/or assist in the execution of the set of schedules, such as through any or all of: providing a set of alerts and/or notifications associated with the set of schedules and/or updated schedules (e.g., patient reminders, technologist reminders, etc.); triggering the receipt of inputs from patients and/or other users (e.g., indicating that the patient is running late but will still attend his or her appointment, providing an estimated time of arrival for the patient, providing an estimated time of arrival for the technologist) (e.g., which can trigger S240); triggering the preparation of a scan and/or exam room; and/or otherwise enabling information to be shared.

S250 preferably involves a set of user interfaces of the system 100 but can additionally or alternative interface with other devices.

4.6 Method: Training the Set of Models S205 and/or Updating the Set of Models S260

The method 200 can include training the set of models S205 (e.g., as described below) and/or updating the set of models S260, which can function to: increase a predictive accuracy of the set of models; continuously learn as more data is acquired; and/or otherwise perform any suitable functions.

In some variants, for instance, an initial set of models is trained in S205 prior to use of the models in S230, where the initial set of models is iteratively updated (e.g., re-trained) based on the set of schedules and/or adjusted schedules produced during iterations of the method 200 and the inputs used to determine the schedules. In some examples, for instance, a final schedule can further be used as training (e.g., re-training) data, where the final schedule reflects what appointments were actually completed and when (e.g., when they actually started, how long they took, when they ended, etc.), thereby providing insight into how accurate the initial and/or adjusted schedules were in prediction.

The models can be trained and/or re-trained based on: a set of goals, reward maximization (e.g., decreasing a difference between the initial schedule and the adjusted schedule, decreasing a difference between a predicted schedule and the final schedule, decreasing an amount of idle time, increasing patient satisfaction, etc.), and/or any other features.

Additionally or alternatively, the method 200 can include any other suitable processes performed in any suitable order.

4.6 Method: Variants

Flowchart for Optimizing Resource Allocation

FIG. 16 illustrates a flowchart of process 1400 for optimizing resource allocation using an allocation optimization system (e.g., allocation system 300 illustrated in FIGS. 5A and/or 5B).

At 1410, scheduled resource allocation data for the first set of resources in a computing environment and contextual information is received. In some aspects, the contextual information may include data for a patient or type of patient, such as historical timeliness data, historical deltas between arrival time and appointment time, patient condition information (e.g., a complexity measure associated with the patient), the type of procedure for which the patient is scheduled, and the like. In some aspects, the resource allocation data may also or alternatively include information about processing resources (e.g., personnel) schedule to perform scheduled procedures during a defined time period, and the contextual information may include information about the processing resources (e.g., experience, efficiency, etc.) can be provided for use in generating an optimized resource allocation. Scheduled resource allocation data and contextual data can be scheduled resource allocation data 310 and contextual data 320 described in FIG. 5A, respectively.

At 1420, using a machine learning model, an optimized allocation of the first set of resources in the computing environment and the second set of resources in the computing environment can be generated based on the scheduled resource allocation data and contextual data. For example, the optimized allocation of resources can be optimization recommendation 338 described in FIG. 5A.

At 1430, the first set of resources and the second set of resources in the computing environment can be allocated based on the generated optimized allocation. For example, resources can be allocated by allocation system 340 described in FIG. 5A. The optimized allocation may be used to generate messaging that modifies and/or creates new time blocks. The messaging may be, for example, scheduling or rescheduling messaging transmitted to one or more health information systems according to a defined message format (e.g., according to messaging formats defined for the Health Level Seven (HL7) standard or other messaging protocols). The scheduling or rescheduling messaging may be used to trigger scheduling of resources used to perform patient procedures and/or schedule processing resources for performing the scheduled patient procedures.

Example Training Scheme for Optimizing Resource Allocation

Figure 6:
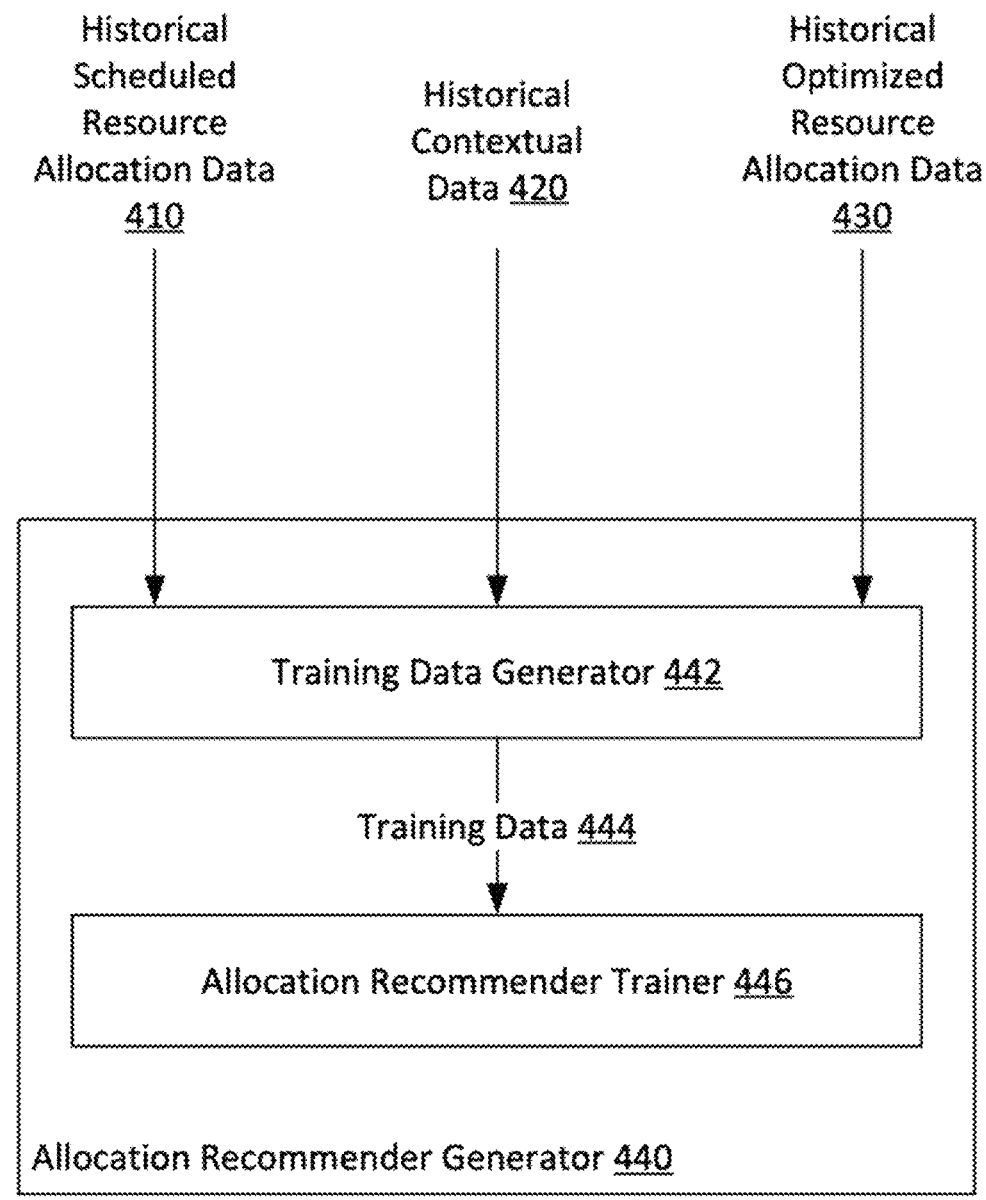
FIG. 6 illustrates an example training scheme to generate an allocation optimization system.

FIG. 6 illustrates an example training scheme 400 to train an allocation optimization system, such as allocation optimization system 300 shown in FIGS. 5A-5B.

Training scheme 400 can use as training data historical scheduled resource allocation data 410, historical contextual data 420, and historical optimized resource allocation data 430. Historical scheduled resource allocation data 410 can be the same or similar to scheduled resource allocation data 310. For example, historical scheduled resource allocation data 410 can include aggregated scheduled resource allocation data 310 from the past. Historical contextual data 420 can be the same or similar to contextual data 320. For example, historical contextual data 420 can include aggregated contextual data 320 from the past. Historical optimized resource allocation data 430 can include sequences of optimized resource allocation by an expert (e.g., an expert human optimizer). For example, historical optimized resource allocation data 430 can include, for each sequence of historical scheduled resource allocation data 410, a sequence of optimized resource allocation.

Historical scheduled resource allocation data 410, historical contextual data 420, and historical optimized resource allocation data 430 can be provided as inputs to allocation recommender generator 440. For example, allocation recommender generator 440 can be used to generate an allocation optimization system, such as allocation optimization system 300 shown in FIG. 3. Allocation recommender generator 440 can include training data generator 442, which can generate training data 444, and allocation recommender trainer 446, which can train the allocation optimization system.

Training data generator 442 can generate training data 444 based on historical scheduled resource allocation data 410, historical contextual data 420, and historical optimized resource allocation data 430. For example, training data generator 442 can parse historical scheduled resource allocation data 410 with corresponding historical contextual data 420 as training inputs, and corresponding historical optimized resource allocation data 430 as desired output (e.g., the label). In some examples, each instance of historical scheduled resource allocation data 410 can include the initial resource allocation scheme for a particular workday (e.g., identified with a date or a weekday), and the corresponding historical contextual data 420 can include information about the scheduled and predicted number of unscheduled patients for that particular workday. Accordingly, corresponding historical optimized resource allocation data 430 can be an optimized sequence of resource allocation for that particular workday. Each parsed data corresponding to a particular workday by training data generator 442 is also known as an instance.

In some examples, training data 444 can include multiple instances, where each instance corresponds to a distinct workday. In some examples, the instances are of varying lengths. For example, for a first workday in the past and a second workday in the past, a different number of patients could appear during the first workday and the second workday. Accordingly, the number of time blocks for resource allocation varies with the number of the patients present. The parsed data can have different lengths corresponding to the different numbers in the different instances.

In some examples, some components in different instances in training data 444 can have a uniform length (e.g., having the same number of elements or components). For example, one or more instances in training data 444 can include data to train the third prediction machine learning model used to predict delay durations for patients discussed in FIG. 1. For example, the data in one or more instances can include information about the historical delay durations of multiple distinct patients. Each of the distinct patients can have a different number of visits and different numbers of historical delay durations. In some examples, to ensure the numbers of historical delay durations are the same for the distinct patients, only the most recent N number of historical delay durations are used, where N can be an integer. In some examples, if all the models to be trained are capable of handling dynamic or sequential inputs, the instances include data of varying lengths.

Training data generator 442 can split the instances of training data 444 into a training set, a validation set, and a test set. The training set can be the sample of data used to fit the models. The models can learn patterns and trends from the training set. The validation set can be the sample of data used to tuning model hyperparameters. The test set can be the sample of data used to provide an unbiased evaluation of a final model fit on the training set.

Training data 444 can be provided as input to allocation recommender trainer 446. Allocation recommender trainer 446 can train allocation optimization systems such as allocation optimization system 300 shown in FIG. 3. In some examples, allocation recommender trainer 446 can pre-load and initialize the allocation optimization system to be trained. In some examples, alternatively, allocation recommender trainer 446 can construct an allocation optimization system based on a set of pre-defined hyperparameters.

Allocation recommender trainer 446 can allocate training data 444 for each component of the allocation optimization system. For example, an allocation optimization system can include a prediction machine learning model (e.g., prediction system 332 shown in FIG. 3) and an optimization machine learning model (e.g., optimization system 336 shown in FIG. 3). Part of training data 444 can be determined by allocation recommender trainer 446 to train the prediction machine learning model while part of training data 444 can be determined by allocation recommender trainer 446 to train the optimization machine leaning model.

In some examples, allocation recommender trainer 446 can train each component of the allocation optimization system in parallel. As described above, the prediction machine learning model in the allocation optimization system can include the first prediction machine learning model and the third prediction machine learning model. Allocation recommender trainer 446 can determine a part of training data 444 to use as training data for the first and the third prediction machine learning models, respectively.

In some examples, the allocation optimization system can include a component machine learning model using outputs from another component machine learning model as inputs. For example, the allocation optimization system can include optimization system 336 using the output from the prediction system 332 (e.g., prediction data 334) as inputs. Accordingly, allocation recommender trainer 446 can first train the prediction system 332 and then the optimization system 336.

In some examples, the prediction system 332 can be trained with standard loss functions for regression and classification problems, such as mean squared error (MSE) and cross-entropy. In some examples, the optimization system 336 can be trained with an objective function with at least one criterion. At least one criterion can include increased resource utilization during a pre-defined time period (e.g., a workday), reduced patient wait time, reduced resource overtime, and reduced delta between the original start time allocated to a resource and optimized start time allocated to the resource.

Example Operations for Predicting Durations of the Resource Allocation

Figure 7:
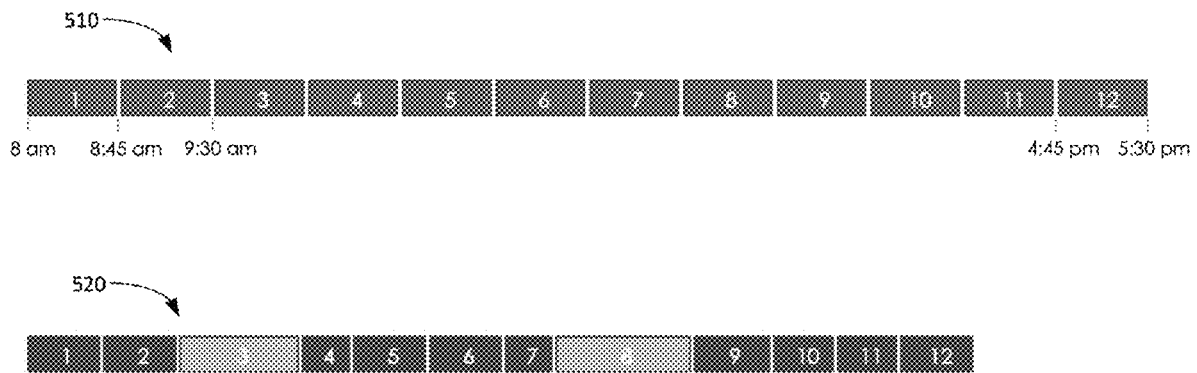
FIG. 7 illustrates example operations for predicting scan time using an allocation optimization system.

FIG. 7 illustrates example operations for predicting durations of the resource allocation using an allocation optimization system (e.g., allocation system 300 illustrated in FIG. 5A or 5B). In some examples, the allocation optimization system includes the first prediction machine learning model as described in FIG. 4, and predicting durations of the resource allocation is performed by the first prediction machine learning model.

Sequence 510 can represent the initial schedule of resource allocation. For example, each of the time blocks 1-12 can represent a time period allocated to a resource to image a patient, scheduled or unscheduled regardless. Although time blocks 1-12 are shown to have uniform durations (e.g., 45 minutes for each block), time blocks in sequence 510 can represent varying durations.

The allocation optimization system can predict the durations of the resource allocation needed for each of the patients to utilize, scheduled and unscheduled (e.g., as shown in FIG. 7). For each of the patients, the allocation optimization system can predict the duration of the resource allocation needed to image the patient. The predicted durations can be aggregated as sequence 520. As illustrated in sequence 520, some patients can require a duration of resource allocation shorter than initially scheduled (e.g., time blocks 1, 2, 4, or the like), whereas some patients can require a duration of resource allocation longer than initially scheduled (e.g., time blocks 3 and 8).

Example Operations for Predicting Missed Resources and Overbooked Resources

Figure 8:
FIG. 8 illustrates example operations for predicting scheduled time block resources that will be unused and overbooking time blocks using an allocation optimization system.

FIG. 8 illustrates example operations for predicting missed appointments and overbooking resources using an allocation optimization system (e.g., allocation system 300 illustrated in FIG. 5A or 5B). In some examples, the allocation optimization system includes the second prediction machine learning model as described in FIG. 4, and predicting missed appointments and overbooking resources are performed by the second prediction machine learning model.

Sequence 610 can represent the initial schedule of resource allocation. Sequence 610 can be the same as or similar to sequence 510 shown in FIG. 7. For example, each of the time blocks 1-12 can represent a duration to use a resource to image each of patients 1-12.

Accordingly, sequence 620 can be the arrangement of time blocks actually happening during a particular workday. For example, time blocks 13 and 14 can represent two durations of resource usage required to image patient 13 and patient 14, respectively. Although time blocks 13 and 14 are shown to have the same duration as time blocks 4 and 10, respectively, time blocks 13 and 14 can have different durations from time blocks 4 and 10.

For time block 4, patient 4 can have a 75% chance of missing the appointment. The allocation optimization system can allow patient 4 and patient 13 to book the same time block for an appointment. Similarly, for time block 10, patient 10 can have a 60% chance of missing the appointment. The allocation optimization system can allow patient 10 and patient 14 to book the same time block for an appointment.

In some examples, some resources can be overbooked for a duration (e.g., in a time block). For example, time block 4 can be booked by more patients, and time block 4 can be overbooked if time block 4 has an expected value of booking patients greater than 1. Accordingly, the allocation optimization system can prevent additional patients from booking time block 4 in an appointment and ask some of the patients who booked time block 4 to reschedule.

In some examples, the allocation optimization system can predict missed appointments and overbook resources using the second prediction machine learning model. As illustrated, the second prediction machine learning model can determine that time block 4 and 10 will be missed. In response, the allocation optimization system can recommend actions to increase the number of resource utilization during a pre-defined time period and reduce patient wait time. For example, the allocation optimization system can recommend, through optimization system 336, for time block 4, admitting patient 13, and for time block 10, admitting patient 14. As a result, sequence 630 can be the optimized resource allocation.

Example Operations for Scan Acquisition

Figure 9:
FIG. 9 illustrates example operations for optimizing scheduled resource allocation based on shortening when the duration of various operations using an allocation optimization system.

FIG. 9 illustrates example operations for increasing scanner utilization based on identifying, by an allocation optimization system (e.g., allocation system 300 illustrated in FIG. 5A or 5B), time slots that can be shortened (e.g., by using a deep learning-based image acquisition and processing). For example, a scan acquisition can be determined with respect to a gap opportunity present (e.g., as shown in FIG. 9).

Sequence 710 can represent the initial schedule of resource allocation. Sequence 710 can be the same as or similar to sequence 510 shown in FIG. 7. For example, each of the time blocks 1-12 can represent a duration to use a resource to treat each of patients 1-12.

Sequence 720 can represent the actual schedule of resource allocation. For example, the durations of resources needed for imaging patients 2, 5, 7, 10, and 12 can be shorter than scheduled. In some examples, the gap opportunity between the end time of imaging of patients 2, 5, 7, 10, and 12 can meet a threshold duration (e.g., 15 minutes).

Sequence 720 can represent the optimized schedule for resource allocation. For example, gap opportunities identified by the allocation optimization system can be used to image additional patients. As illustrated, gap opportunities after optimized time block 2, 5, 7, 10, and 12 can be used to form new time blocks 13-17, which can be used to image additional patients 13-17, respectively.

Example Operations for Utilizing Open or On-Hold Resources

Figure 10:
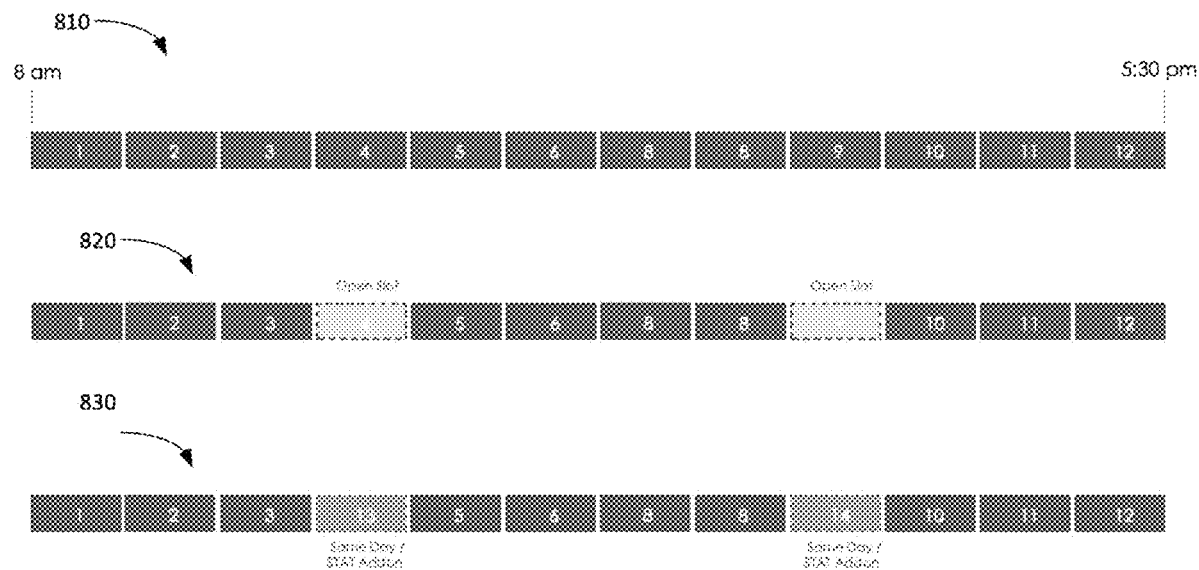
FIG. 10 illustrates example operations for utilizing open or on-hold resources using an allocation optimization system.

FIG. 10 illustrates example operations for utilizing open or on-hold resources using an allocation optimization system. For example, open or on-hold resources can be defined with respect to one or more hyperparameters in an allocation optimization system.

Sequence 810 can represent the initial schedule of resource allocation. Sequence 810 can be the same as or similar to sequence 510 shown in FIG. 7. For example, each of the time blocks 1-12 can represent a duration to use a resource to image each of patients 1-12.

Sequence 820 can represent the schedule of resource allocation with open or on-hold resources. For example, time blocks 4 and 9 can be designated as open slots (e.g., time block) by the allocation optimization system. Open resources can be used for unscheduled tasks and offers more flexibility.

Sequence 830 can represent the optimized schedule of resource allocation. For example, open slots 4 and 9 can be used to image additional patients, such as patient 13 and patient 14.

Example Operations for Updating Resources

Figure 11:
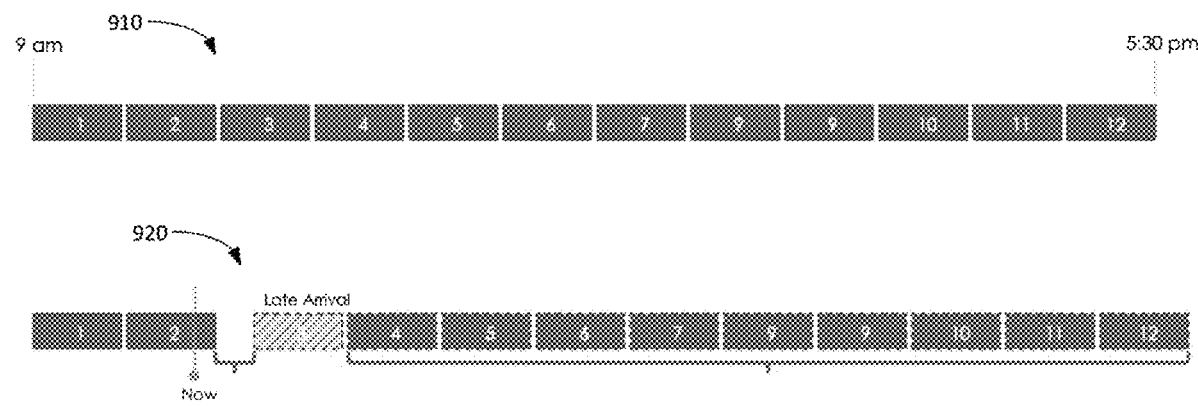
FIG. 11 illustrates example operations for real-time updating of resources using an allocation optimization system.

FIG. 11 illustrates example operations for updating resources using an allocation optimization system (e.g., allocation system 300 illustrated in FIGS. 5A and/or 5B).

Sequence 910 can represent the initial schedule of resource allocation. Sequence 910 can be the same as or similar to sequence 510 shown in FIG. 7. For example, each of the time blocks 1-12 can represent a duration to use a resource to image each of patients 1-12.

Sequence 910 can represent the actual schedule in real-time. For example, the allocation optimization system can have a current state in time block 2 by an optimization system in the allocation optimization system. Near the end of time block 2, the allocation optimization system can transition into a current state in time block 3. For example, patient 3 can be late for an appointment for time block 3. Accordingly, the allocation optimization system can determine actions to take for time block 3 as output recommendations (e.g., as shown in FIG. 11).

Sequentially, the allocation optimization system can transition the current state into subsequent time blocks 4-12 and determine actions to take for each of the subsequent time blocks 4-12.

Example Optimized Resource Allocations

Figure 12:
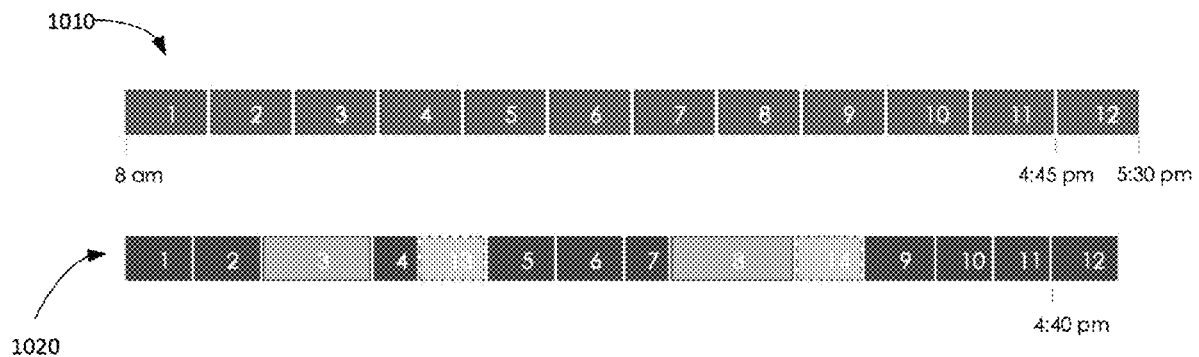
FIG. 12 illustrates example operations for optimizing resource allocation using an allocation optimization system.

FIG. 12 illustrates an example optimized resource allocation generated using an allocation optimization system (e.g., allocation system 300 illustrated in FIGS. 5A and/or 5B).

Sequence 1010 can represent the initial schedule of resource allocation. Sequence 1010 can be the same as or similar to sequence 510 shown in FIG. 7. For example, each of the time blocks 1-12 can represent a duration to use a resource to image each of patients 1-12.

Sequence 1020 can represent the optimized schedule of resource allocation using the allocation optimization system. For example, sequence 1020 can have increased amount of resource utilization during a pre-defined time period (e.g., a workday), reduced wait time for resource utilization, reduced resource overtime, and reduced delta between original start time allocated to a resource and optimized start time allocated to the resource as compared to sequence 1010.

Figure 13:
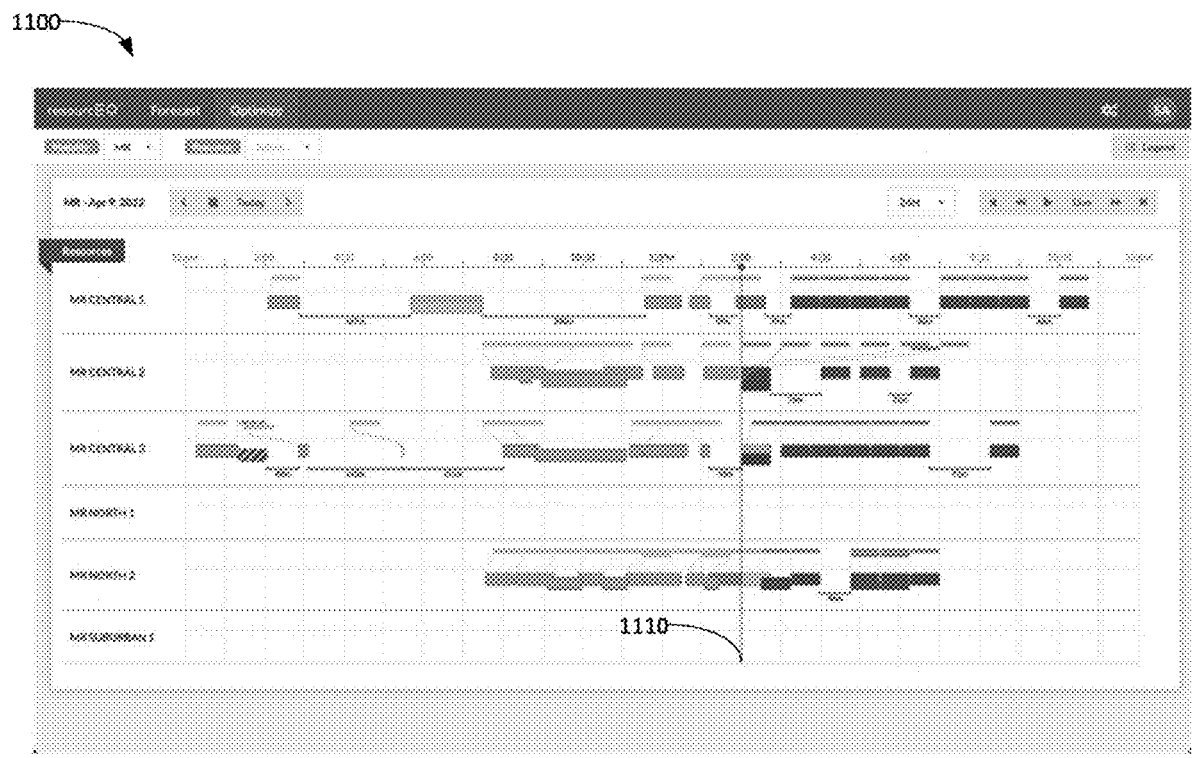
FIGS. 13, 14, and 15 illustrate example resource allocation and forecast data generated by optimizing a resource allocation in a computing environment using a decision-making subsystem configured as an allocation optimization system.

FIG. 13 illustrates an example of an optimized resource utilization schedule 1100 generated using an allocation optimization system (e.g., allocation system 300 illustrated in FIGS. 5A and/or 5B). In this example, the resources for which a schedule is optimized includes a plurality of device resources (e.g., medical imaging devices) in different locations (designated "Central", "North", and "Suburban"). Scheduling data to the left of current time marker 1110 generally reflects historical schedule and usage data for the current day. In this example, it can be seen that large gaps exist in resource usage overnight (e.g., until 8:00 AM), and after 8:00 AM, a number of appointments have been scheduled, and the time resources have been used on various device resources.

Scheduling data to the right of current time marker 1110 generally reflects a projected, optimized utilization of the device resources through the end of the day. In this example, it may be seen that some time blocks may be overbooked to account for appointments for patients who may not actually appear for those appointments. Further, the optimization generated by the allocation optimization system may include a plurality of open slots, which may be generated based on aggregating differences between a priori defined time blocks and projected durations for each of the scheduled procedures and shifting the start times of appointments to generate these open time slots. For example, as illustrated, a 39 minute open slot and two 46 minute open slots is generated/projected for the device at MR Central 1, a 76 minute and a 31 minute open slot is generated/projected for the device at MR Central 2, and a 91 minute open slot is generated/projected for the device at MR Central 3. Further, while some amount of open time exists between the end of the appointment 2:00 PM and the beginning of the 3:00 PM appointment, this amount of open time may be insufficient to generate a slot in which a procedure can be performed, and thus, this amount of open time may not be designated as an available slot. As discussed, these open slots may be kept open for unscheduled procedures to be performed using the resources across which scheduling is optimized using the allocation optimization system.

Figure 14:
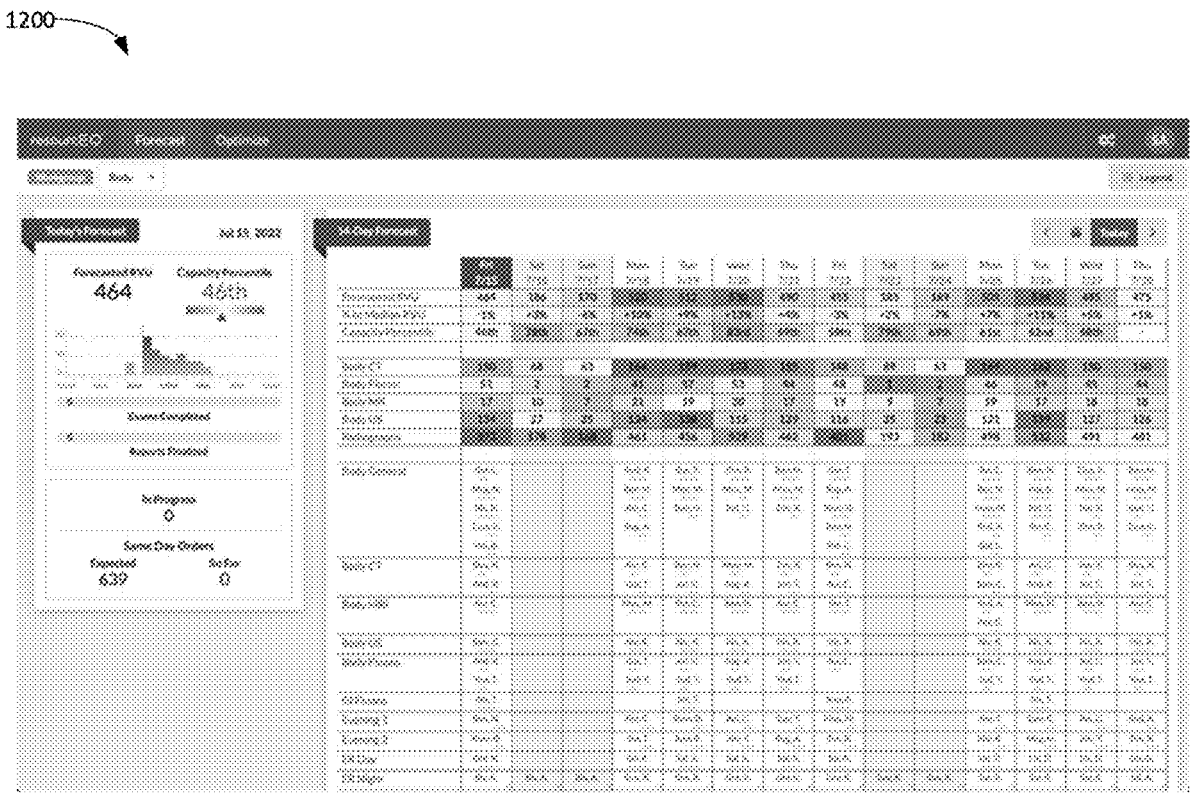

FIG. 14 illustrates an example of a resource utilization forecast 1200 generated based on an optimized resource schedule generated using an allocation optimization system (e.g. allocation system 300 illustrated in FIGS. 5A and/or 5B). In this example, a total amount of work, defined in terms of a number of procedures and a forecasted aggregate complexity (e.g., an aggregate relative value unit (RVU) calculated as the sum of RVU values defined for each procedure included in the optimized resource schedule). Generally, the forecast may be generated based on an optimization of resources (e.g., scheduling of processing resources) that attempts to avoid an overcapacity scenario in which the forecast aggregate complexity is greater than the total available capacity to perform procedures on any given day. In some aspects, the forecast 1200 may graphically illustrate information about capacity utilization for each type of procedure for which operations are scheduled and the forecast aggregate complexity. Generally, where the graphical illustration indicates that a resource utilization is over a median percentile for a given type of procedure or the aggregate complexity, a system that generates forecast 1200 may color the cells associated with these types of procedures and/or aggregate complexity to inform a user that certain resources may be overloaded or may be approaching an overloaded state. Likewise, where the graphical illustration indicates that a resource utilization is below a median percentile, the system that generates forecast 1200 may color the cells associated with these types of procedures and/or aggregate complexity to inform a user that certain resources may be underutilized or may be approaching an underutilized state. These graphical illustrations can be used, for example, as a prompt for additional resources to be allocated (for scenarios in which resources are overloaded or approaching an overloaded state) or a prompt to remove resources (for scenarios in which resources are underutilized or approaching an underutilized state). Additionally or alternatively, the overcapacity can reflect and/or be determined based on a forecasted aggregate procedure volume and/or workload. For instance, the overcapacity can reflect the amount of calculated workload (e.g., number of procedures to be performed, number of cases to be analyzed, etc.) that exceeds an amount able to be performed by the set of users and/or resources (e.g., at the facility).

Figure 15:
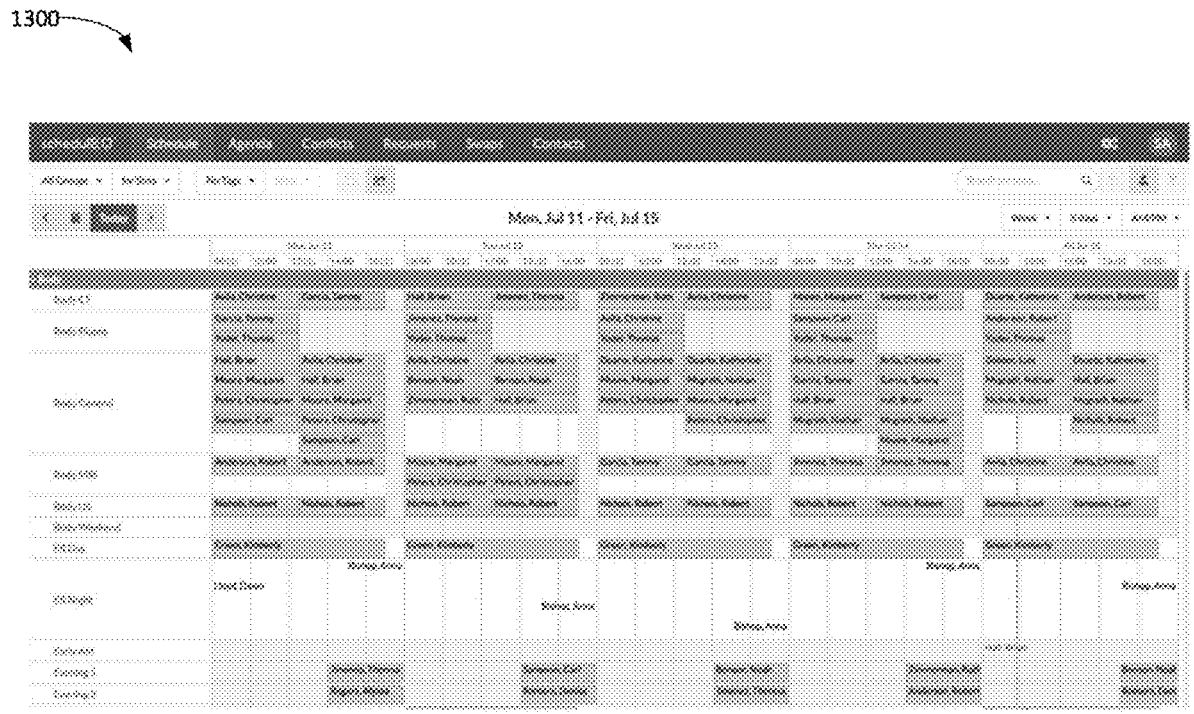

FIG. 15 illustrates an example of a processor resource schedule 1300 generated based on an optimized resource schedule generated using an allocation optimization system (e.g. allocation system 300 illustrated in FIGS. 5A and/or 5B). In this example, the processor resources allocated during each day (or discrete block of time) may be allocated based on the projected/optimized allocation of resources so that the capabilities of the assigned processor resources match (with a minimal amount of overcapacity or undercapacity) the estimated aggregate capacity of the procedures scheduled during any given time period. Generally, the scheduling of processing resources may be constrained based on a total amount of time any processor can be scheduled over a time period (e.g., a daily and weekly total scheduled time constraint), the aggregate complexity of the scheduled procedures during any given time period, and capabilities of each processor. In some aspects, schedule 1300 may further be constrained by a maximum number of processing resources that can be assigned to perform specific types of procedures.

The preceding description is provided to enable any person skilled in the art to practice the various aspects described herein. The examples discussed herein are not limiting of the scope, applicability, or aspects set forth in the claims. Various modifications to these aspects will be readily apparent to those skilled in the art, and the generic principles defined herein may be applied to other aspects. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

The invention claimed is:

1. A method for modifying objects of a graphical display corresponding to adjustments to a temporal schedule associated with a facility, the method comprising:
   determining an initial temporal schedule, the initial temporal schedule comprising a first set of booked time slots associated with appointments of a first set of users;
   at a user interface, rendering the graphical display based on the initial temporal schedule, wherein the graphical display comprises a set of objects corresponding to a set of device resources comprising medical imaging devices positioned at a set of geographical locations;
   receiving a set of appointment requests, associated with usage of the set of objects corresponding to the set of device resources, from a second set of users, wherein the initial temporal schedule is unable to accommodate the set of appointment requests;

collecting a set of contextual inputs for use in adjusting the initial temporal schedule;

evaluating the initial temporal schedule and the set of contextual inputs with a set of multiple trained neural network models to produce a set of outputs, the set of multiple trained neural network models comprising:

a first set of trained neural network models configured to:
predict a set of durations associated with the first set of booked time slots;
predict a set of delays associated with the first set of booked time slots;
predict a set of idle times in the initial temporal schedule;

a second set of trained neural network models configured to, for each of the first set of booked time slots:
predict a likelihood that the booked time slot will be missed by a user of the first set;

training, at least one of the set of multiple trained neural network models, based on reward maximization;

creating a set of temporal gap opportunities in the initial temporal schedule based on the set of outputs, comprising:

decreasing a duration of a first portion of the first set of booked time slots, comprising, at the graphical display of the user interface, automatically decreasing a length of objects and coloring objects of the set of objects corresponding to medical imaging devices of the set of devices associated with the first portion of the first set of booked time slots;

adjusting a start time of a second portion of the first set of booked time slots, comprising, at the graphical display of the user interface, automatically moving objects of the set of objects corresponding to medical imaging devices of the set of devices associated with the second portion of the first set of booked time slots; and overbooking a third portion of the first set of booked time slots, comprising, at the graphical display of the user interface, automatically stacking objects of the set of objects corresponding to medical imaging devices associated with at least one of a first or second booked time slot in the third portion;

automatically adjusting the initial temporal schedule to produce a revised temporal schedule based on the set of gap opportunities, comprising filling the set of temporal gap opportunities with the set of appointment requests to create a second set of booked time slots; and re-training at least one of the set of multiple trained neural network models based upon the revised temporal schedule and data reflecting a set of completed appointments of the set of appointment requests, wherein re-training comprises reinforcement of at least one of the set of multiple trained neural network models whenever a new set of contextual inputs is received.

2. The method of claim 1, wherein the set of contextual inputs comprises:
supplementary information associated with the first set of users;
environmental information associated with the facility; and
historical information associated with the facility.

3. The method of claim 2, wherein the set of contextual inputs further comprises historical information associated with the facility, comprising:
which days of the week have a highest average volume of appointments; and
an efficiency level of a third set of users, the third set of users performing a set of tasks associated with the first and second sets of booked time slots.

4. The method of claim 1, further comprising, upon completion of each of the first and second sets of booked time slots, iteratively refining the revised temporal schedule.

5. The method of claim 4, wherein iteratively refining the revised temporal schedule comprises evaluating a most recent revised temporal schedule and an end time of a completed appointment slot with the set of multiple trained neural network models.

6. The method of claim 1, further comprising aggregating adjacent gap opportunities and filtering out a subset of gap opportunities from further consideration upon comparison of each of the subset of gap opportunities with a predetermined threshold.

7. The method of claim 1, wherein the initial temporal schedule is further adjusted based supplementary information associated with the second set of users.

8. The method of claim 1, wherein overbooking the third portion of the first set of booked time slots comprises assigning multiple users to each of the third portion time slots, wherein each of the multiple users is associated with a historical score below a predetermined threshold, the historical score associated with a likelihood of attending a scheduled appointment.

9. The method of claim 1, wherein each of the second set of trained neural network models has a different architecture than that of the first set of trained neural network models.

10. The method of claim 1, further comprising iteratively retraining at least a portion of the set of multiple trained neural network models based on a final schedule, wherein the final schedule is determined based on a set of recorded times associated with a time period at the facility.

11. The method of claim 1, wherein training, at least one of the set of multiple trained neural network models, comprises organizing training data into a training set, a validation set, and a test set, and tuning model hyperparameters based upon the validation set.

12. A non-transitory computer-readable medium storing instructions that, when executed by a computer, cause the computer to:
determine an initial schedule associated with a facility, the initial schedule comprising a $1^{st}$ set of tasks, wherein the initial schedule is unable to comprise a $2^{nd}$ set of tasks;
at a user interface, render a graphical display of the $1^{st}$ set of tasks wherein the graphical display comprises a set of objects corresponding to a set of device resources comprising medical imaging devices positioned at a set of geographical locations;
collect a set of contextual inputs configured to be used in adjusting the initial schedule;
evaluate and train a set of trained neural network models based on the initial schedule and the set of contextual inputs to produce a set of prediction outputs;
create a set of temporal gap opportunities relative to the initial schedule based on the set of prediction outputs, comprising:
based on an adjusted duration and a delay relative to a start time of each of the $1^{st}$ set of tasks, determine a projection for the $1^{st}$ set of tasks, wherein a graphical display of the projection for the $1^{st}$ set of tasks is positioned vertically offset from the graphical display of the $1^{st}$ set of tasks, wherein determining the projection for the $1^{st}$ set of tasks comprises:

decreasing a duration of a projection for a first portion of the $1^{st}$ set of tasks, comprising, at the graphical display of the user interface, automatically decreasing a length of objects and coloring objects of the set of objects corresponding to medical imaging devices of the set of devices associated with the projection for the first portion;

increasing a duration of a projection for a second portion of the $1^{st}$ set of tasks, comprising, at the graphical display of the user interface, automatically increasing a length of objects of the set of objects corresponding to medical imaging devices of the set of devices associated with the projection for the second portion;

adjusting a start time of the projections for the first and second portions, comprising, at the graphical display of the user interface, automatically moving objects of the set of objects corresponding to medical imaging devices of the set of devices associated with the projections for the first and second portions, wherein graphical markers connect start times of the $1^{st}$ set of tasks to start times of the projection for the $1^{st}$ set of tasks;

overbooking a projection for a third portion of the $1^{st}$ set of tasks, comprising, at the graphical display of the user interface, automatically moving objects of the set of objects corresponding to medical imaging devices of the set of devices associated with the projection for at least one of a first or second task in the third portion of the $1^{st}$ set of tasks such that the first and second tasks are vertically stacked;

produce the set of temporal gap opportunities based on the projection for the $1^{st}$ set of tasks;

automatically adjust the initial schedule to produce a revised schedule based on the set of gap opportunities, comprising assigning the $2^{nd}$ set of tasks to the set of temporal gap opportunities; and re-train at least one of the set of trained neural network models based upon performing reward maximization involving the initial schedule and the revised schedule, wherein re-training comprises reinforcement of at least one of the set of trained neural network models whenever a new set of contextual inputs is received.

13. The computer-readable medium of claim 12, wherein the set of contextual inputs is associated with:
the $1^{st}$ set of users; and
the facility.

14. The computer-readable medium of claim 12, wherein the set of prediction outputs comprises, for each of the $1^{st}$ set of booked appointment tasks, wherein each of the $1^{st}$ booked tasks is associated with a start time and a duration:
an adjusted duration of the booked task;
a delay relative to the start time; and
a likelihood of the booked task being unattended.

15. The computer-readable medium of claim 12, wherein the computer-readable medium further causes the computer to, upon completion of each of the first and second sets of tasks, iteratively refine the revised temporal schedule.

16. The computer-readable medium of claim 15, wherein iteratively refining the revised temporal schedule comprises, for each of the first and second sets of tasks, evaluating a most recent revised temporal schedule and an end time of the task when completed with the set of multiple trained neural network models.

17. The computer-readable medium of claim 12, wherein overbooking the third portion of the first set of tasks comprises assigning multiple users to each of the third portion time slots, wherein each of the multiple users is associated with a historical score below a predetermined threshold, the historical score associated with a likelihood of an associated user attending the task.

18. The computer-readable medium of claim 17, wherein the computer-readable medium further causes the computer to adjust the historical score of a user based on a final schedule associated with the facility, wherein the final schedule is determined based on a set of recorded times associated with a time period at the facility.

19. The computer-readable medium of claim 12, wherein the set of trained neural network models comprises multiple trained neural network models, wherein at least a first portion of the set of trained neural network models has a different architecture than a second portion of the set of trained neural network models.

* * * * *